(12) United States Patent
Zamft et al.

(10) Patent No.: US 12,260,938 B2
(45) Date of Patent: Mar. 25, 2025

(54) MACHINE LEARNING DRIVEN GENE DISCOVERY AND GENE EDITING IN PLANTS

(71) Applicant: HERITABLE AGRICULTURE INC., Mountain View, CA (US)

(72) Inventors: Bradley Zamft, Mountain View, CA (US); Vikash Singh, Los Angeles, CA (US); Mathias Voges, Cupertino, CA (US); Thong Nguyen, Pasadena, CA (US)

(73) Assignee: HERITABLE AGRICULTURE INC., Mountain View, CA (US)

( * ) Notice: Subject to any disclaimer, the term of this patent is extended or adjusted under 35 U.S.C. 154(b) by 294 days.

(21) Appl. No.: 17/207,169

(22) Filed: Mar. 19, 2021

(65) Prior Publication Data
US 2022/0301658 A1  Sep. 22, 2022

(51) Int. Cl.
*G16B 40/00*  (2019.01)
*G16B 5/20*  (2019.01)

(52) U.S. Cl.
CPC .............. *G16B 40/00* (2019.02); *G16B 5/20* (2019.02)

(58) Field of Classification Search
CPC .................................. G16B 40/00; G16B 5/20
See application file for complete search history.

(56) References Cited

U.S. PATENT DOCUMENTS

| | | | |
|---|---|---|---|
| 11,618,896 B2 * | 4/2023 | Zhang | C12N 15/102 435/440 |
| 2014/0220568 A1 | 8/2014 | Inze et al. | |

(Continued)

FOREIGN PATENT DOCUMENTS

WO  2021035164 A1  2/2021

OTHER PUBLICATIONS

Wu et al., "Scalable Planning with Deep Neural Network Learned Transition Models", Journal of Artificial Intelligence Research, Jul. 2020, vol. 68, https://doi.org/10.1613/jair.1.11829, 571-606 (Year: 2020).*

(Continued)

*Primary Examiner* — Karlheinz R. Skowronek
*Assistant Examiner* — Emilie A Neulen
(74) *Attorney, Agent, or Firm* — Kilpatrick Townsend & Stockton LLP

(57) ABSTRACT

The present disclosure relates to leveraging explainable machine learning methods and feature importance mechanisms as a mechanism for gene discovery and furthermore leveraging the outputs of the gene discovery to recommend ideal gene expression profiles and the requisite genome edits that are conducive to a desired phenotype. Particularly, aspects of the present disclosure are directed to obtaining gene expression profiles for a set of genes measured in a tissue sample of a plant, inputting the gene expression profiles into a prediction model constructed for a task of predicting a phenotype as output data, generating, using the prediction model, the prediction of the phenotype for the plant, analyzing, by an explainable artificial intelligence system, decisions made by the prediction model to predict the phenotype, and identifying a set of candidate gene targets for the phenotype as having a largest contribution or influence on the prediction based on the analyzing.

20 Claims, 11 Drawing Sheets

(56) References Cited

U.S. PATENT DOCUMENTS

2018/0285520 A1  10/2018  Butruille et al.
2020/0202241 A1*  6/2020  Abeliuk ............... G16B 40/00

OTHER PUBLICATIONS

Arsham Ghahramani, Fiona M. Watt, Nicholas M. Luscombe; "Generative adversarial networks simulate gene expression and predict perturbations in single cells"; bioRxiv 262501; Jul. 30, 2018; doi: https://doi.org/10.1101/262501 (Year: 2018).*

Lundberg, Scott M., and Su-In Lee. "A unified approach to interpreting model predictions." Advances in neural information processing systems 30 (2017). (Year: 2017).*

Borrill et al., "Identification of Transcription Factors Regulating Senescence in Wheat Through Gene Regulatory Network Modelling", Plant Physiololgy, vol. 180, Jul. 2019, 16 pages.

Jin et al., "Auto-Keras: An Efficient Neural Architecture Search System", Applied Data Science Track Paper, 2019, 11 pages.

Kannan et al., "Combining Gene Network, Metablolic and Leaf-Level Models Shows Means to Future-Proof Soybean Photosynthesis Under Rising $CO_2$", In Silico Plants, vol. 1, Issue 1, 2019, 18 paages, pages.

Kawakatsu et al., "Epigenomic Diversity in a Global Collection of *Arabidopsis thaliana* Accessions", Cell 166, Jul. 16, 2016, 15 pages.

Perez-Enciso et al., "A Guide on Deep Learning for Complex Trait Genomic Prediction", Genes, 10, 553,, Jul. 2019, 19 pages.

Vats et al., "Genome Editing in Plants: Exploration of Technological Advancements and Challenges", Cells, 8 (11), 1386, Nov. 4, 2019, 39 pages.

Wang et al., "Deep Learning for Plant Genomics and Crop Improvement", Current Opinion in Plant Biology, retrieved from www.science direct.com, 2020, 8 pages.

Harfouche et al., "Accelerating Climate Resilient Plant Breeding by Applying Next-Generation Artificial Intelligence", Trends in Biotechnology, vol. 37, No. 11, Jun. 21, 2019, pp. 1217-1235.

International Application No. PCT/US2021/060694, International Search Report and Written Opinion, Mailed On Mar. 7, 2022, 15 pages.

Mlone et al., "Explainable Artificial Intelligence: a Systematic Review", arxiv.org, Available Online at URL: https://arxiv.org/abs/2006.00093, May 2020, 81 pages.

* cited by examiner

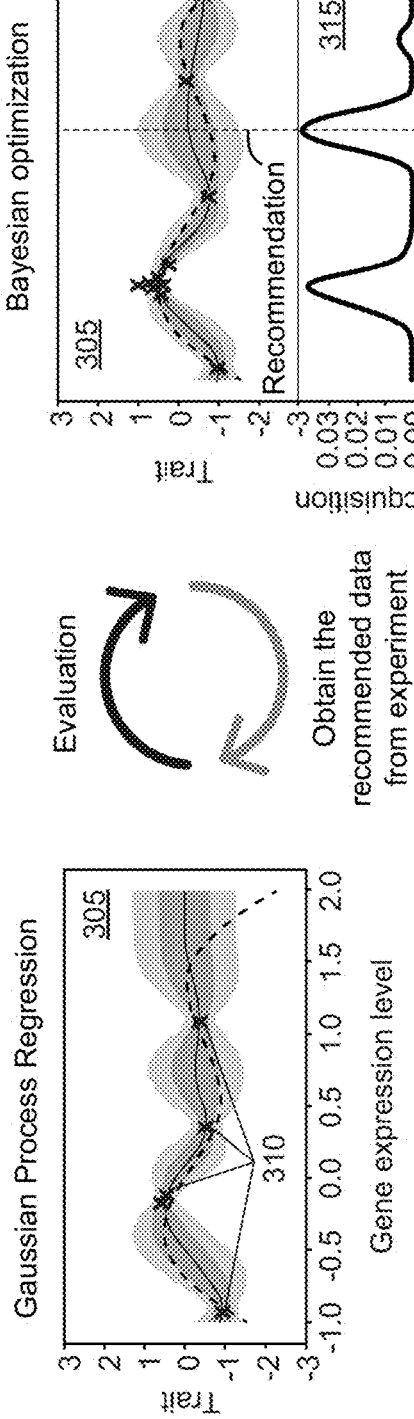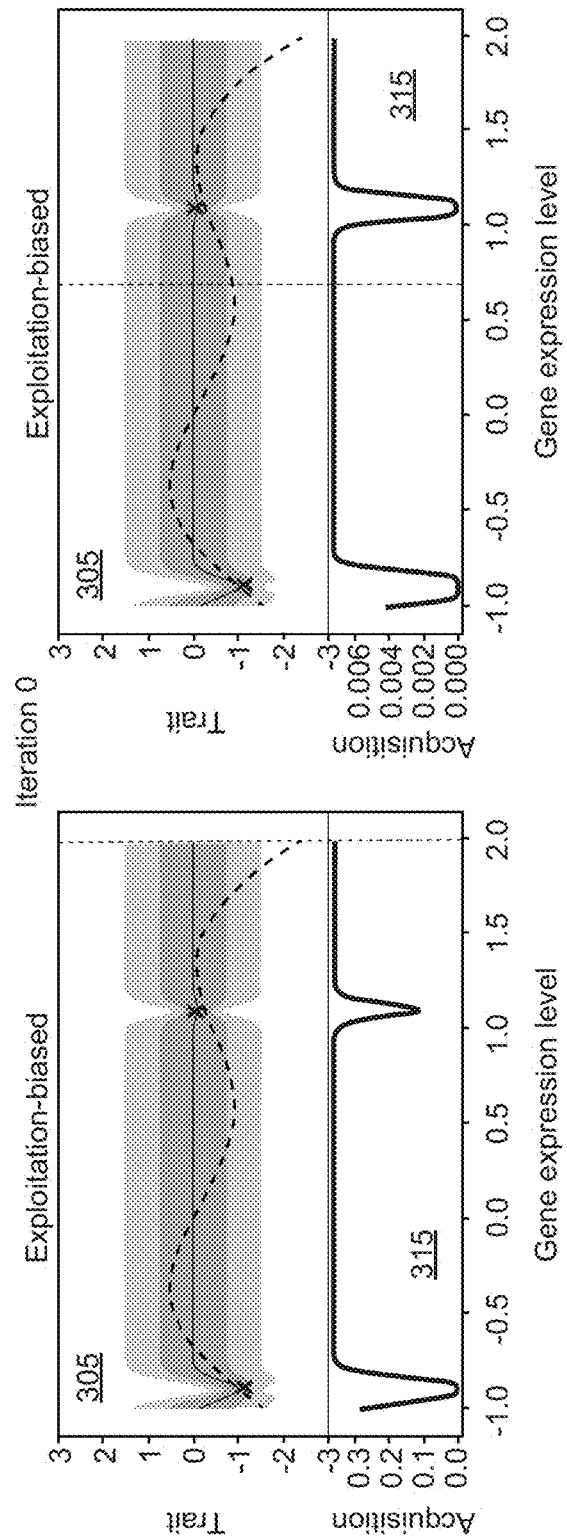
FIG. 3A
FIG. 3B

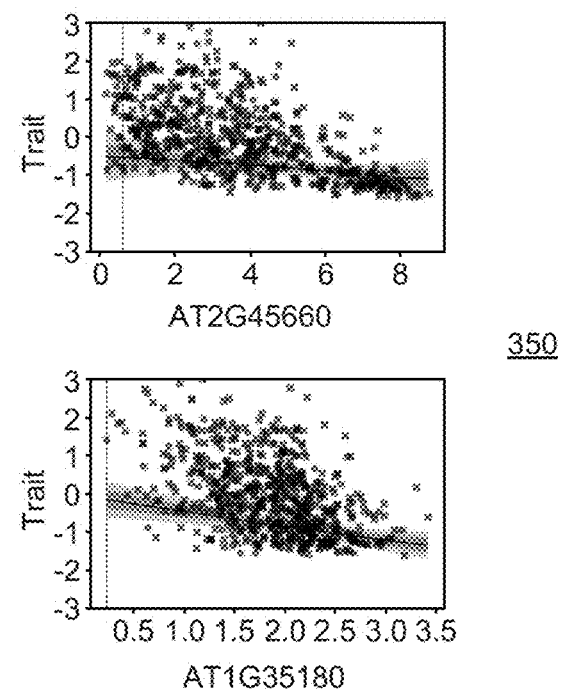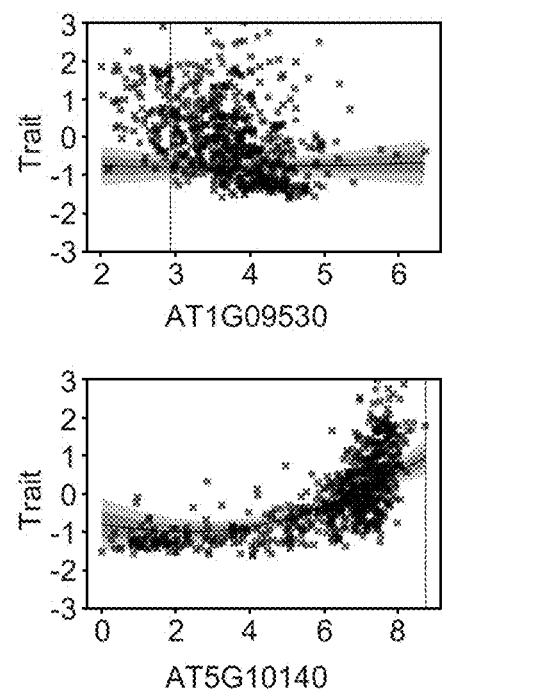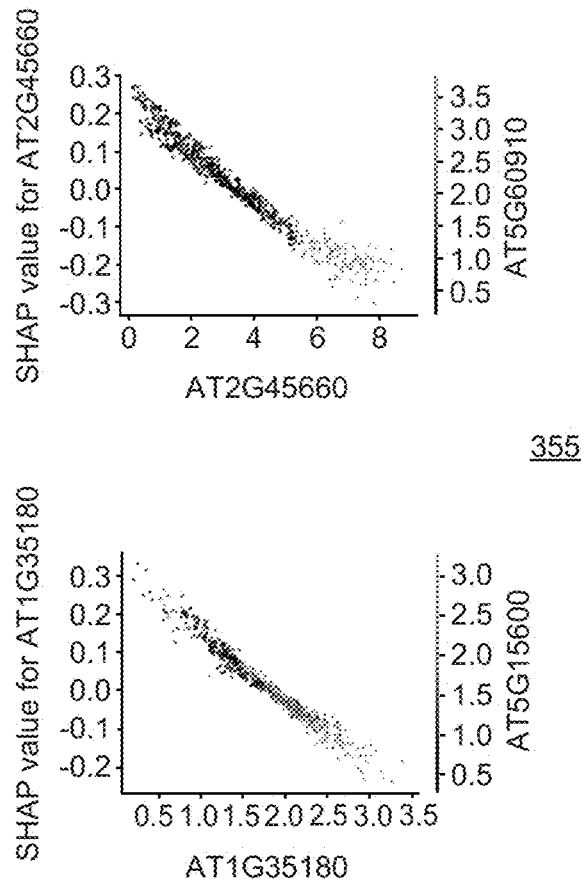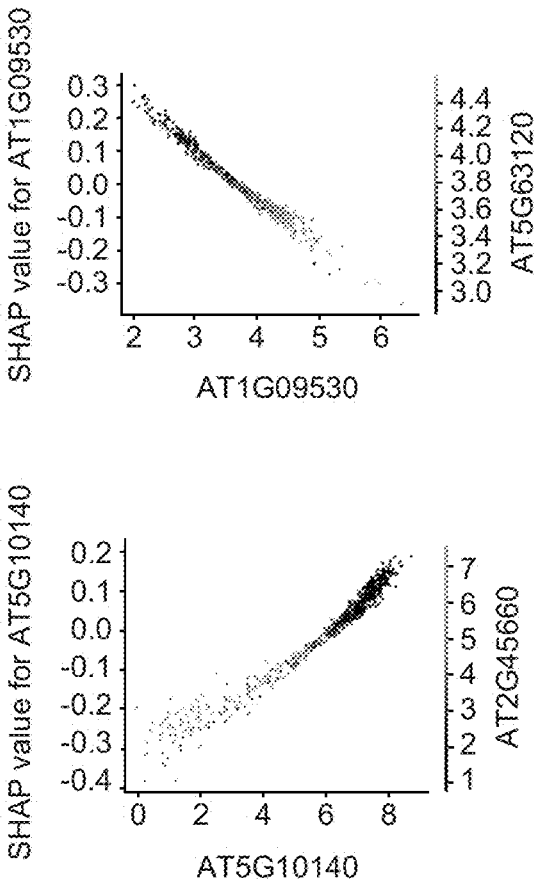
FIG. 3C

Initial Results (SHAP Genes)

| Gene | Min | Max | Mean | Rec (LR) | Rec (DNN) | Samp1 (DNN) | Samp2 (DNN) | Samp3 (DNN) |
|---|---|---|---|---|---|---|---|---|
| AT2G45660 | 2.58 | 13.57 | 8.23 | 2.77 | 2.78 | 3.91 | 5.83 | 5.81 |
| AT5G62165 | 0 | 9.44 | 4.12 | 0.16 | 0.87 | 1.0 | 0.0 | 2.58 |
| AT5G44590 | 0 | 7.45 | 2.79 | 7.07 | 7.19 | 3.81 | 5.29 | 6.29 |
| AT3G52480 | 4.39 | 8.65 | 6.97 | 5.78 | 4.65 | 5.17 | 5.09 | 5.70 |
| DTF1 | 23.5 | 139.0 | 63.32 | NA | NA | 110.5 | 87.75 | 103.75 |

Suggestions:
Upregulate AT5G44590 (Bash repressor transcriptions factors)
Downregulate AT2G45660, AT2G45660, AT3G52480 (Bash activator transcription factors)

Gene: Selected plant genes derived from the DNN+SHAP pipeline
Min: Minimum Log Transformed Expression of Gene
Max: Maximum Log Transformed Expression of Gene
Mean: Mean Log Transformed Expression of Gene
Rec (LR): Recommended expression for adversarial attack on LR
Rec (DNN): Recommended expression for adversarial attack on DNN
Samp1/2/3 (DNN): Expression profiles of closest samples in dataset to DNN recommendation

FIG. 6

MACHINE LEARNING DRIVEN GENE DISCOVERY AND GENE EDITING IN PLANTS

FIELD

The present disclosure relates to plant genome editing, and in particular to leveraging explainable machine learning methods and feature importance mechanisms (both on neural networks and other nonlinear models) as a mechanism for gene discovery and furthermore leveraging the outputs of these gene discovery models to recommend ideal gene expression profiles, including the requisite genome edits, that are conducive to a desired phenotype.

BACKGROUND

Genetic diversity is primarily a function of sexual recombination and mutagenesis, and is an important means for trait improvement in plants. For example, genetic diversity in plant genetic resources provides opportunity for plant breeders to develop new and improved cultivars with desirable characteristics, which include both farmer-preferred traits (e.g., high yield potential, large seed, etc.) and breeder-preferred traits (e.g., pest and disease resistance and photosensitivity, etc.). For thousands of years, plant domestication relied on natural genetic variability via evolutionary forces (e.g., selection, mutation, migration, genetic drift, etc.) to select for favorable genetic changes. Plant domestication or artificial selection favors a few alleles at the cost of others resulting in increased frequency of selected alleles. Consequently, plant domestication reduces the genetic diversity when compared to the diversity in the wild. Furthermore, the generation of genetic variants via evolutionary forces was completely uncontrolled and largely dependent on the environment of plant cultivation.

In order to gain some control over genetic diversity and create new varieties, breeders have used different techniques to analyze the genetic diversity of plants and use that analysis to introduce heritable mutations into plant genomes. For example, morphological, cytological, biochemical, and molecular marker characterization combined with various statistical tools (e.g., multivariate statistics) can be used to assess the genetic diversity among different strains, varieties, or entries of a species. These techniques have been used in the assessment of genetic divergence, classification of germplasm into different groups, and in the selection of diverse parents to develop hybrid phenotypes such as transgressive segregants. However, the more knowledge that is obtained about the underlying genomic factors of yield and quality from the diversity analysis, the more the limitations of traditional breeding approaches become apparent. Due to the random nature of recombination and undirected mutagenesis, further improvement of select germplasm is a lengthy and tedious process that is often impaired by linkage drag, the transfer of deleterious genetic material genetically linked to a desirable trait. Thus, the reliance on natural or randomly induced diversity is a limiting factor slowing down the conventional breeding process and contributing to unpredictable breeding outcomes.

In the past century, the use of various mutagens (e.g., chemical compounds and irradiation) facilitated the rapid generation of large pools of genetic variation, which could then be used to speed up the breeding process. However, these methods have several drawbacks, including the non-specific nature of the generated mutations, the large amount of nucleotides simultaneously mutated, and at times the deletion, duplication or rearrangement of large genomic fragments. As a consequence, the identification of mutations of interest via random mutagenesis is a long and labor-intensive process. The development of sequence-specific engineered endonucleases, the mega-nucleases, zinc finger nucleases (ZFNs), transcription activator-like effector nucleases (TALENs) and type II clustered regularly interspaced short palindromic repeat (CRISPR)/CRISPR-associated protein 9 (Cas9), have provided tools for targeted gene editing (targeted mutagenesis) in plant genomes. These programmable nucleases enable the generation of single or double-stranded DNA breaks (DSBs) in a site-specific manner. In eukaryotic cells, the induced DSBs can be repaired either via the error-prone end-joining pathway or via the error-free homology-directed repair (HdR) pathway. Both pathways are harnessed to introduce gene modifications at the target loci. Nonetheless, conventional genetic diversity analysis remains limiting for gene discovery and the identification of gene modifications that are conducive to a desired phenotype. Thus, despite the enormous potential of CRISPR and other gene editing tools, significant challenges remain if this potential is to be fully realized.

SUMMARY

In various embodiments, a method is provided that comprises: obtaining a set of gene expression profiles for a set of genes measured in a tissue sample of a plant; inputting the set of gene expression profiles into a prediction model constructed for a task of predicting a phenotype as output data by a nonlinear algorithm learning relationships or correlations between features of gene expression profiles and the phenotype; generating, using the prediction model, the prediction of the phenotype for the plant based on the relationships or the correlations between the features of the set of gene expression profiles and the phenotype; analyzing, by an explainable artificial intelligence system, decisions made by the prediction model to predict the phenotype, where the analyzing comprises: (i) generating a set of feature importance scores for the features used in the prediction of the phenotype, and (ii) ranking or otherwise sorting the features based on the feature importance score associate with each of the features; identifying, based on the ranked or otherwise sorted features, a set of candidate gene targets for the phenotype as having a largest contribution or influence on the prediction; and identifying, based on the identified set of candidate gene targets, a set of genomic regions that when edited provide a requisite change in a gene expression profile to realize an expected phenotypic change.

In some embodiments, the explainable artificial intelligence system uses SHapley Additive exPlanations, DeepLIFT, integrated gradients, Local Interpretable Model-agnostic Explanations (LIME), Attention-Based Neural Network Models, or Layer-wise Relevance Propagation to analyze the decisions made by the prediction model.

In some embodiments, the method further comprises: the identifying the set of genomic regions comprises inputting the set of candidate gene targets into a gene edit model constructed for a task of modeling gene edits of the set of candidate gene targets, and identifying, based on the modeled gene edits, an optimal set of genetic targets for genome editing one or more gene within the set of candidate gene targets, thus maximizing, minimizing, or otherwise modulating the phenotype; and generating, using the gene edit model, an ideal gene expression profile for the phenotype based on the optimal genetic targets for the genome editing of one or more genes within the set of candidate gene targets.

In some embodiments, the explainable artificial intelligence system uses SHapley Additive exPlanations, which generates a set of Shapley values as the feature importance scores for the features used in the prediction of the phenotype; the Shapley values represent estimates of each features importance as well as a direction; and the gene edit model models the gene edits by ascertaining directionality of regulation directly from the Shapley values.

In some embodiments, the prediction model is a Gaussian process model; and the gene edit model models the gene edits using a Bayesian optimization algorithm comprising two components: (i) the Gaussian process model of an underlying Gaussian process function, and (ii) an acquisition function for sampling various data points.

In some embodiments, the prediction model is a deep neural network; and the gene edit model models the gene edits by performing an adversarial attack on the deep neural network, the adversarial attack comprising freezing the weights of the deep neural network, and optimizing over a space of constrained inputs to maximize or minimize the phenotype.

In some embodiments, the method further comprises: comparing the ideal gene expression profile to a naturally occurring distribution of gene expression for the plant; determining a gene edit recommendation for upregulating or downregulating a particular gene, a sub group of genes, or each gene within the ideal gene expression profiles based on the comparing; and making, using a gene editing system, a genetic edit or perturbation to a genome of the plant in accordance with the gene edit recommendation.

In some embodiments, a system is provided that includes one or more data processors and a non-transitory computer readable storage medium containing instructions which, when executed on the one or more data processors, cause the one or more data processors to perform part or all of one or more methods disclosed herein.

In some embodiments, a computer-program product is provided that is tangibly embodied in a non-transitory machine-readable storage medium and that includes instructions configured to cause one or more data processors to perform part or all of one or more methods disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

BRIEF DESCRIPTION OF THE DRAWINGS

The present disclosure will be better understood in view of the following non-limiting figures, in which:

FIGS. 3A and 3B show use of a Gaussian process model and Bayesian optimization for modeling gene edits in accordance with various embodiments;

FIG. 3C shows results of gene edit modeling using Bayesian optimization as compared to using Shapley values in accordance with various embodiments;

FIG. 6 shows an example of an ideal gene expression profile determined using an adversarial based modeling approach in accordance with various embodiments;

Figure 1:
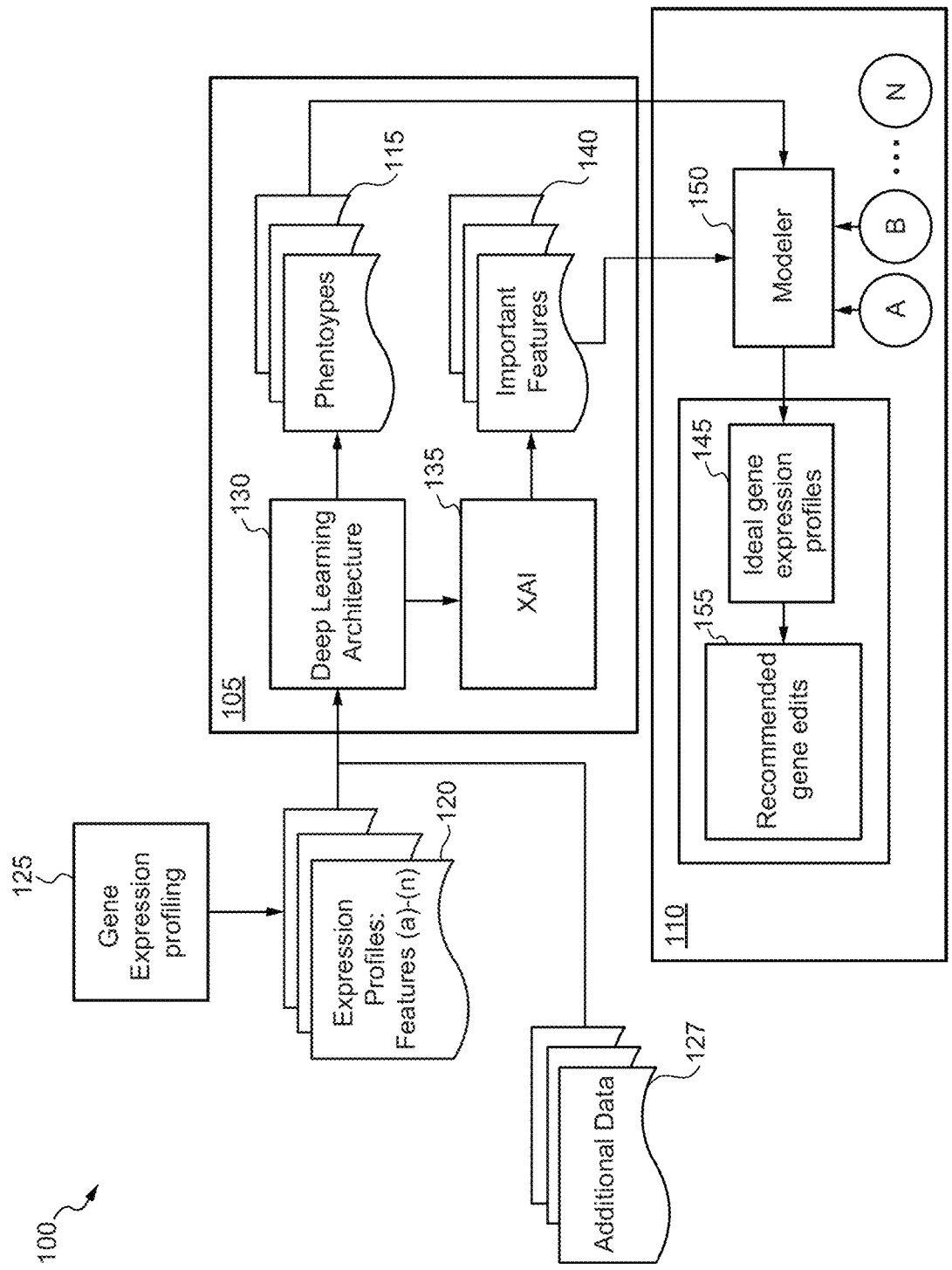
FIG. 1 show block diagrams of a machine learning pipeline for both gene discovery and gene editing in plants according to various embodiments.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart or diagram may describe the operations as a sequential process, many of the operations may be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination may correspond to a return of the function to the calling function or the main function.

I. Introduction

Understanding the underlying biological mechanisms governing particular phenotypes in plants has traditionally required lengthy iterations of experimentation. Such experimentation has included genetic manipulation (such as gene knockout and overexpression via gene delivery systems) and pharmacological targeting of critical molecular signaling pathways. This process is especially time and resource intensive for organisms in which the molecular mechanisms are largely unexplored and the process of building up a significant portfolio of knowledge about these mechanisms has historically taken the scientific community decades.

The traditional computational approaches for associating particular base-pair differences in genomes, called single nucleotide polymorphisms (SNPs), in the organism's genome with a particular phenotype have been based on genome-wide association studies (GWAS) and quantitative trait loci (QTL) analysis. GWASs are used to associate particular genetic variants with a particular phenotype through a statistical analysis of naturally occurring genomic samples with a distribution of that particular phenotype. QTL analysis is similar to GWAS in that the ultimate goal is to associate phenotypic variation with particular regions of the genome, though rather than observing natural variation in a population, QTLs target two genetically contrasting strains with regards to a particular phenotype and analyze the first (F1) and second (F2) generation offspring. While GWAS and QTL analysis have made tremendous strides in identifying interesting candidate SNPs that have been subsequently validated, some weaknesses of GWAS and QTL analysis is their weakness in modeling complex nonlinear interactions (such as epistasis), identifying causal SNPs, and identifying SNPs of weak effect sizes.

To take advantage of more sophisticated nonlinear machine learning methods for GWAS and QTL analysis, attention has recently been drawn to deep learning architectures. Deep learning architectures such as deep neural networks (DNN), deep belief networks, recurrent neural networks (RNN) and convolutional neural networks (CNN) have been applied to technical fields including computer vision, machine vision, speech recognition, natural language processing, audio recognition, bioinformatics, and machine translation, where they have produced results comparable to and in some cases surpassing human performance. While deep learning architectures have been applied and demonstrated some success in a variety of prediction tasks involving GWAS and QTL datasets (e.g., risk prediction), a primary concern in their real-world application and deployment is the lack of inherent explainability due to the black-box nature of the algorithms used in these networks. Thus, the genetic architectures and variances of most plant phenotypes remain largely unexplained.

To address these limitations and problems, a machine learning pipeline is disclosed herein for both gene discovery and gene editing in plants with an overarching goal of obtaining granular control of plant phenotypes. The pipeline may be decomposed into two separate components. For the first component, potentially relevant genes in a given plant species for a particular phenotype can be identified through explainable artificial intelligence methods (XAI). More specifically, machine learning models (nonlinear) which predict phenotype values using gene expression profiles as inputs can be inspected via XAI to identify the genes which have the largest influence on the predictive models. These top genes as identified by XAI on the predictive models serve as candidate genes to be involved in the molecular regulatory processes for that particular plant species and phenotype. For the second component, given the top genes targeted to be involved in the manifestation of a particular phenotype, modeling techniques can be applied to generate suggestions on the regulation of those particular genes. More specifically, the second component of the pipeline makes both coarse and fine grained recommendations on the directionality of regulation (up/down regulation), which can be translated into actionable edits that can be taken via methods in synthetic biology.

In one exemplary embodiments, a method is provided that comprises: obtaining a set of gene expression profiles for a set of genes measured in a tissue sample of a plant; inputting the set of gene expression profiles into a prediction model constructed for a task of predicting a phenotype as output data by a nonlinear algorithm learning relationships or correlations between features of gene expression profiles and the phenotype; generating, using the prediction model, the prediction of the phenotype for the plant based on the relationships or the correlations between the features of the set of gene expression profiles and the phenotype; analyzing, by an explainable artificial intelligence system, decisions made by the prediction model to predict the phenotype, where the analyzing comprises: (i) generating a set of feature importance scores for the features used in the prediction of the phenotype, and (ii) ranking or otherwise sorting the features based on the feature importance score associate with each of the features; and identifying a set of candidate gene targets for the phenotype as having a largest contribution or influence on the prediction based on the ranked features. The method may further comprise identifying, based on the identified set of candidate gene targets, a set of genomic regions that when edited provide the requisite change in a gene expression profile to realize the expected phenotypic change. The identifying the set of genomic regions may comprise inputting the set of candidate gene targets into a gene edit model constructed for a task of modeling gene edits of the set of candidate gene targets, and identifying, based on the modeled gene edits, a set of optimal genetic targets for genome editing each gene within the set of candidate gene targets, thus maximizing or minimizing the phenotype. The method may further comprise generating, using the gene edit model, an ideal gene expression profile for the phenotype based on the optimal set of genetic targets for the genome editing of each gene within the set of candidate gene targets.

II. Machine Learning Pipeline

FIG. 1 shows a block diagram of a machine learning pipeline 100 for both gene discovery and gene editing in plants, in accordance with various embodiments. The machine learning pipeline 100 comprises a first component 105 for gene discovery in plants via explainable artificial intelligence and second component 110 for modeling gene edits in plants using machine learning. The first component 105 comprises a model architecture configured to predict a particular phenotype 115 of a given plant from gene expression profiles 120. A phenotype of a given plant describes the collective expression of the genotype in conjunction with the environment on a plant's observable characteristics. Plant height, biomass, bud density, leaf shape, color, fruit or grain production, drought resistance, insect resistance, and the like are all examples of phenotypic characteristics (discrete and continuous variation) that can vary with different growing conditions, even within the same genotype. The model architecture is trained to output a response variable indicative of a prediction of the phenotype 115. In some instances, the phenotype 115 is a binary, ordinal, or continuous phenotype, and the output layer of the model architecture uses nonlinear activation functions according to the type of response variable best suited for identifying the phenotype 115 (e.g., hyperbolic tangent or linear functions may be used for continuous phenotypes, sigmoid for binary phenotypes, and softmax for ordinal or multiclass phenotypes). In certain instances, the particular phenotype 115 being predicted is a continuous phenotype and the output layer of the model architecture uses a nonlinear activation function such as the hyperbolic tangent function to generate a response variable for identifying the continuous phenotype 115.

A plant's cells modulate the levels of expression of the genes they contain depending on external and internal signals. Controlling the expression levels of various genes enables each cell to control its size, shape and functions. The ways in which a plant's cells express the genes they contain affects the plant's phenotype, e.g., resistance to a given insect or draught, or whether it will produce sweet fruit or tart fruit. Gene expression profiling 125 measures which genes are being expressed in cells at any given moment. This is because cell gene expression is influenced by external and internal stimuli, including whether the cell is dividing, what factors are present in the cell's environment, the signals it is receiving from other cells, and even the time of day. In order to determine which genes are being expressed, gene expression profiling 125 measures the amount of mRNA levels, showing the pattern of genes expressed by each cell at the transcription level. In some instances, this means measuring relative mRNA amounts in two or more experimental conditions, then assessing which conditions resulted in specific genes being expressed. Different techniques may be used to measure the amount of mRNA levels and determine gene expression. In some instances, the mRNA levels are measured via microarray analysis, reverse transcription polymerase chain reaction (RT-PCR), through next generation sequencing of cDNA—the DNA that results from a reverse transcription reaction of the tissue's purified RNA (RNA-seq), or any combination thereof.

The gene expression profiling 125 outputs the gene expression profiles 120 comprising features (a)-(n) for a fixed set of genes measured in a particular tissue in the plant at a particular time in its development cycle. If a gene is being used by a cell of the tissue to make mRNA at the particular time, the gene is considered 'on' within the gene expression profiles 120; and if the gene is not being used by the cell of the tissue to make mRNA at the particular time, the gene is considered 'off' within the gene expression profiles 120.

In some instances, the gene expression profiles are transformed into a set of numerical representations of gene expression (e.g., log-transformed gene expression profiles) for the fixed set of measured genes in a given tissue at a particular time point in which the tissue was sampled. In some instances, additional data 127 is generated for input with the gene expression profiles into the model architecture of the first component 105 as described in greater detail herein (e.g., input data can be obtained from an environment and management practices system, a cultivation system, a multi-omics system, and/or a modeling system). The additional data 127 may include: (i) data concerning the environmental conditions under which the plant is exposed to up to any given moment (e.g., the moment when the amount of mRNA levels was measured), and (ii) data concerning the maintenance conditions under which the plant is exposed to up to any given moment (e.g., the moment when the amount of mRNA levels was measured). The environmental conditions include location-specific environmental conditions the plant is exposed to, e.g. temperature, precipitation, soil properties, and the like. The maintenance conditions include any adjustable aspect of the management of the growth of the plant, e.g., inputs such as fertilizer or water, the timing of planting, fertilizing, harvesting, and the like.

Traditional models for genomic prediction in plant biology have either been linear models (linear regression) or linear mixed effect models such as ridge regression best linear unbiased prediction (rrBLUP). While it is known that the underlying processes contributing to the various phenotypes in plants (especially those that are heavily polygenic) are inherently nonlinear, many of the traditional modeling methodologies take a strictly linear form. Even some of the most fundamental equations governing biochemical systems, such as the Hill, Monod, and Michaelis-Menten equations, are generally nonlinear. Yet the majority of approaches aimed at genomic prediction have used linear methods, for the simple reasons that they are computationally tractable and have built in interpretability through the inspection of the linear coefficients. Interpretability is not naturally given when using more complex modeling methodologies such as deep neural networks.

Nonetheless, since more expressive, nonlinear models are better suited for modeling the inherent nonlinear nature of biological systems, the model architecture for predicting a phenotype 115 is a deep learning architecture 130, which serves as a more powerful predictive model when provided a large number of samples exhibiting large genetic variation (e.g., as with gene expression profiles 110). In some instances, the deep learning architecture 130 is a deep neural network (i.e., two or more hidden layers); however, it should be understood that the teachings herein are applicable to both neural networks and other nonlinear models implemented singularly, as a plurality such as an ensemble, or in combination. The deep learning architecture 130 is constructed for the task of predicting a phenotype as the output data by learning relationships or correlations between features of the input data (gene expression profiles 110) and the phenotype. Specifically, the deep learning architecture 130 is constructed in a manner that forces an algorithm to learn how to capture nonlinear patterns in hidden layers and produce the outputs in terms of probabilities (e.g., binary classification) or predicted response variables in an interval (e.g., for continuous response) by the use of one or more activation functions. The weights that govern linear transformations which are subsequently passed to nonlinear activation functions are learned in a training process from a set of labeled samples (e.g., training data comprising sets of gene expression profiles labeled with phenotype ground truths).

Figure 2A:
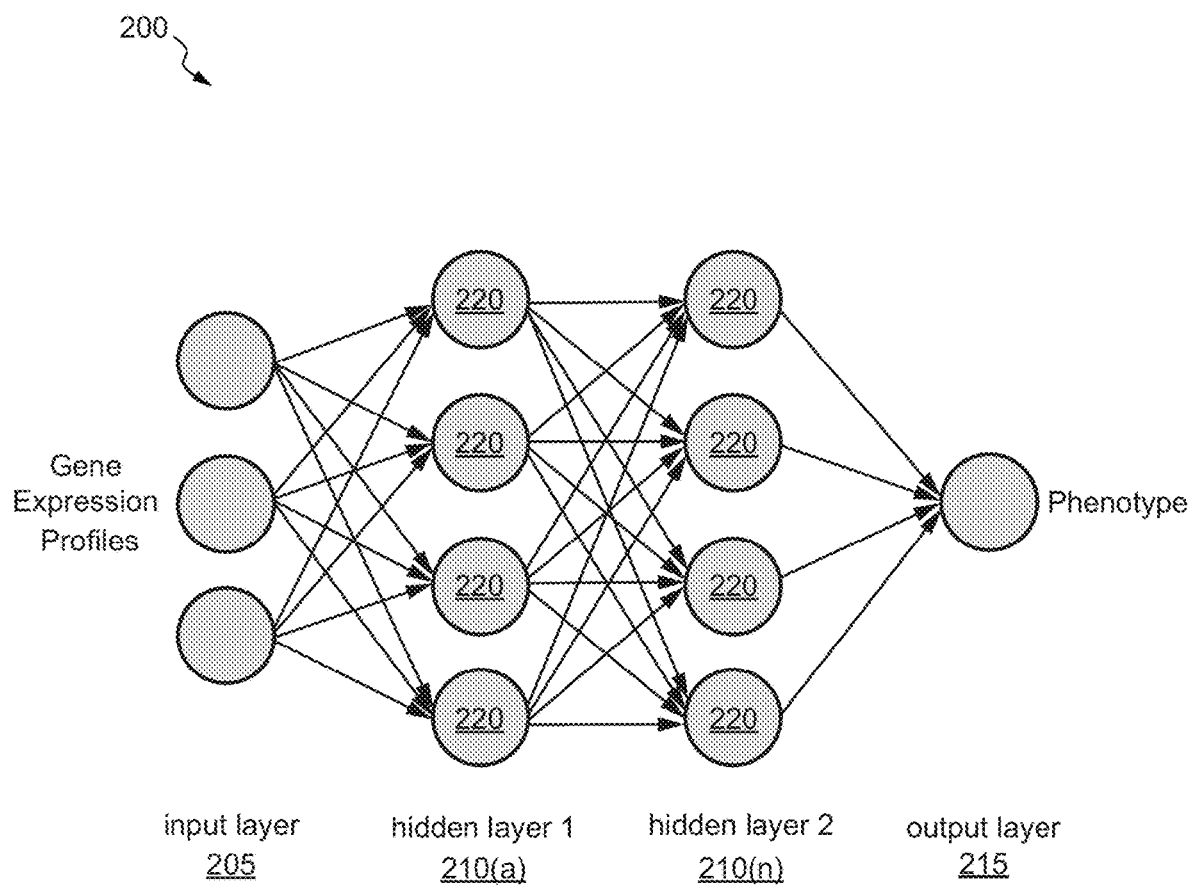
FIG. 2A shows an exemplary deep neural network in accordance with various embodiments.

FIG. 2A shows an exemplary deep neural network 200 (in this instance the exemplary deep neural network is a feedforward neural network; however, it should be understood that other types of neural networks could be implemented without departing from the spirit and scope of the present disclosure). The deep neural network 200 comprises an input layer 205, multiple hidden layers 210(a)-210(n), and an output layer 215. The input layer 205 is used to feed the input data or features to the deep neural network 200. In some instances, the input data or features is gene expression profiles or a transformed version thereof, e.g., log-transformed gene expression profiles. The deep neural network 200 applies a series of functions to the input data using the multiple hidden layers 210($a$)-210($n$). The number of hidden layers defines the depth of the deep neural network 200. By having multiple hidden layers 210($a$)-210($n$), the deep neural network 200 can compute complex functions by cascading simpler functions. In some instances, the depth of the deep neural network 200 is two or more hidden layers. In certain instances, the depth of the deep neural network 200 is two hidden layers, as depicted in FIG. 2A.

Each node 220 in the multiple hidden layers 210($a$)-210($n$) is a neuron, which are the basic processing units of the deep neural network 200. The processing of neurons may be implemented in two steps—(1) each neuron calculates the weighted sum of its inputs and weights, and (2) each node applies a transformation called an activation function to produce the output. The neurons in each layer receive the output of the neurons in the previous layer as input. The strength of a connection is called the weight, which is a weighting factor that reflects its importance. The weights are the parameters which the network has to learn during the training phase. If a connection has zero weight, a neuron does not have any influence on the corresponding neuron in the next layer. The impact is excitatory when the weight is positive, or inhibitory when the weight is negative. Thus, a deep neural network can be seen as a directed acyclic graph (DAG) whose nodes correspond to neurons and whose edges correspond to the links between them. Each neuron receives, as input, a weighted sum of the outputs of the neurons connected to its incoming edges. The activation function is used as a decision making component at the outgoing edges of the neurons. The activation functions can be linear or nonlinear, determine the type of output (continuous, binary, categorical and count) of the deep neural network 200, and are important for capturing nonlinear patterns of the input data. Examples of activation functions include the linear activation function, the rectifier linear unit (ReLU), the leaky ReLU, the sigmoid activation function, the softmax activation function, hyperbolic tangent activation function, and the exponential activation function.

The output layer 215 outputs a response variable indicative of a prediction (e.g., a particular phenotype). The activation function to be used in the output layer is different for different problems. For a binary classification problem, the output needs to be either 0 or 1. Thus, a sigmoid activation function may be used. For a multiclass classification problem, a softmax activation function may be used. For a regression problem, where the output is not a predefined category, a linear unit activation function may be used. In some instances, the particular phenotype is a binary, ordinal, or continuous phenotype, and the output layer 215 uses nonlinear activation functions according to the type of response variable best suited for identifying the particular phenotype (e.g., hyperbolic tangent function may be used for continuous phenotypes, sigmoid for binary phenotypes, and softmax for ordinal or multiclass phenotypes). In certain instances, the particular phenotype being predicted is a continuous phenotype and the output layer 215 uses a nonlinear activation function such as the hyperbolic tangent function to generate a response variable for identifying the particular continuous phenotype.

The training phase for the deep neural network 200 includes selecting hyperparameters for the deep neural network 200 (e.g., selecting the number of hidden layers or activation function(s)), performing iterative operations of inputting data sets from training data into the deep neural network 200 to find a learned set of parameters (e.g., weights and/or biases) that minimizes the loss or error function for the deep neural network 200, and validating or testing network with the learned set of parameters. The hyperparameters are settings that can be tuned or optimized to control the behavior of the deep neural network 200. Most neural networks explicitly define hyperparameters that control different aspects of the networks such as memory or cost of execution. However, additional hyperparameters may be defined to adapt a network to a specific scenario. For example, the hyperparameters may include the number of hidden layers of the network, number of neurons in hidden layers, the learning rate of a network, or type of activation function(s) for the network. Defining hyperparameters may be challenging, and thus a tuning process may be used for defining an optimal set of hyperparameter values for the specific scenario. The hyperparameter tuning comprises a value search process that may include selecting a combination of values for the hyperparameters from a grid of values with different hyperparameter combinations. The aforementioned value search process can either be exhaustive or leverage more intelligent optimization techniques such as Bayesian optimization or genetic algorithms.

To implement the hyperparameter tuning process, network training, and testing/validation processes, the training data may be acquired, divided into sets, and preprocessed (e.g., annotated with ground truth labels). For example, training data may be generated by acquiring sets of gene expression profiles for one or more phenotypes, preprocessing the sets of data, splitting the sets of data into a training set (for training the network to learn the learnable parameters) (e.g., 70%), a tuning set (for tuning hyper-parameters and selecting the optimal non-learnable parameters) (e.g., 15%), and a testing or validation set (for estimating the generalization performance of the network) (e.g., 15%), and annotating the subset of data with ground truth labels. In some instances, the training data is gene expression profiles with ground truth labels or a transformed version thereof, e.g., log-transformed gene expression profiles with ground truth labels.

The sets of data may be acquired and split using a validation technique such as K-Fold Cross-Validation, Leave-one-out Cross-Validation, Leave-one-group-out Cross-Validation, Nested Cross-Validation, or the like. For example, K-Fold Cross-Validation may be used where k−1 folds are used for the training (outer training) and the remaining fold for testing. Then inside each fold with the corresponding training, k-fold cross-validation is used, and k−1 folds are used for training (inner training) and the remaining fold for tuning evaluation. The network for each hyper-parameter combination in the grid is trained with the inner training data set, and the combination in the grid with the lower prediction error is selected as the optimal hyper-parameter in each fold. Then if the sample size is small using the outer training set, the network is fitted again with the optimal hyper-parameter. Finally, with these estimated model parameters (weights and/or bias), the predictions for the testing set are obtained. This process is repeated in each fold and the average prediction performance of the k testing set is reported as prediction performance. In some instances, the predictions for the testing set are evaluated versus the ground truth using correlation techniques such as Bland-Altman method and the Spearman's rank correlation coefficients and calculating performance metrics such as the error, accuracy, precision, recall, receiver operating characteristic curve (ROC), etc.

Each iteration of the training process for the deep neural network 200 can involve inputting data sets from the training and/or tuning set and learning a set of model parameters (configured with a defined set of hyperparameters) so that the value of the loss or error function (e.g., modified cross entropy loss) using the set of model parameters is smaller than the value of the loss or error function using a different set of model parameters in a previous iteration. The loss or error function can be constructed to measure the difference between the labels/ground truth and the inferred data such as an inferred phenotype for a set of gene expression profiles. Initial values (e.g., random values or values selected based on prior knowledge) are assigned to the set of model parameters to be used as a starting point for training the deep neural network 200, and each iteration of the training process for deep neural network 200 can further involve feeding the loss backwards through the network (i.e., backpropagation) to fine tune the set of model parameters. This process of iteratively passing batches of data through the deep neural network 200, estimating error based on the subset of the training dataset, and updating the weights, so that the error is decreased, is known as Gradient Descent. As used herein, when an action is "based on" something, this means the action is based at least in part on at least a part of the something. Once the set of model parameters of the deep neural network 200 have been trained by optimizing the loss or error function the network is able to predict the phenotype of an unseen genotype from a set of gene expression profiles. In addition to tracking the training loss, the testing loss can additionally be tracked in order to implement early stopping, which halts training of a deep neural network when a clear divergence between training and testing loss is noted. The early stopping process combats overfitting, preventing scenarios in which the neural network performs extremely well on the training data at the expense of generalizing to validation data.

The number of examples of data from the training set used in the estimate of the error gradient is the batch size and is an important hyperparameter that influences the dynamics of the learning algorithm. Training the deep neural network 200 can be challenging as it can be sensitive to the initial set of model parameters and configuration of the learning algorithm. A reason for this challenge is the distribution of the inputs to layers deep in the network may change after each batch of data when the set of model parameters are updated. This can cause the learning algorithm to persistently chase a moving target (known as internal covariate shift). In some instances, to overcome this challenge, batch normalization is used for training the deep neural network 200. Batch normalization may be performed by scaling the output of each hidden layer 210, e.g., standardizing the activations of each input variable per batch of data, such as the activations of a node from the previous layer. Standardizing the activations of the prior layer means that assumptions the subsequent layer makes about the spread and distribution of inputs during the weight update will not change, at least not dramatically. This stabilizes the learning process and reduces the number of training epochs (speeds up training) required to train the deep neural network 200.

As should be understood, other training-tuning-validation mechanisms are contemplated and may be implemented. For example, the deep neural network 200 may be trained and hyperparameters may be tuned on data from a first subset of data and the data from a second subset of data may only be used for testing and evaluating performance of the model. Moreover, although the training-tuning-validation mechanisms described herein focus on training a new deep neural network 200. These training-tuning-validation mechanisms can also be utilized to fine tune existing deep neural networks 200 trained from other datasets. For example, in some instances, a deep neural network 200 might have been pre-trained using gene expression profile data for a first phenotype. In those cases, the deep neural network 200 can be used for transfer learning and retrained/validated using new sets of gene expression profiles for a second phenotype.

Alternative to the feedforward neural network described with respect to FIG. 2A, an exemplary learning architecture 130 implemented in some embodiments is a graph neural network (GNN). GNNs are neural networks that are able to process input data encoded as general undirected/directed labeled graphs (a data structure comprised of two components: nodes (vertices) and edges), and provide a way to perform node-level, edge-level, and graph-level prediction tasks. Consequently, in such embodiments, the gene expression profiles 120 are configured as a graph structured representation of the genes in the plant species. Given graph structured representation of the genes where each node represents a gene and each edge represents a gene-gene interaction, the GNN converts the nodes to recurrent units and the edges to feed-forward neural networks. The GN then performs Neighborhood Aggregation for all nodes n number of times and performs global pooling over the embedding vectors of all nodes to get graph representation H. The graph representation H is then passed to high layers where it is used to predict the phenotype 115 for the gene expression profiles 120.

Alternative to a deep neural network such as the DNN or GNN described herein, an exemplary deep learning architecture 130 implemented in some embodiments is a nonlinear model such as Gaussian process model. The Gaussian process model is a generalization of the Gaussian probability distribution and can be used as the basis for non-parametric machine learning algorithms for classification and regression tasks. Machine-learning algorithms that involve a Gaussian Process can be implemented in the deep learning architecture 130 using lazy learning and a measure of the similarity between points (the kernel function) can be used to predict the value for an unseen point (e.g., the phenotype 115 for the gene expression profiles 120) from training data. The prediction is not just an estimate for that point, but also has uncertainty information and expressed as a one-dimensional Gaussian distribution. For multi-output predictions, multivariate Gaussian processes may be used, for which the multivariate Gaussian distribution is the marginal distribution at each point.

In order to generate candidate gene targets for the phenotype 115 of interest, XAI techniques are applied to obtain the importance of each feature for all predictions in a holdout data set or a new set of input data (i.e., a set of gene expression profiles 120). In some instances, the deep learning architecture 130, which predicts the phenotypes 115, using gene expression profiles 120 as inputs is analyzed via XAI 135 to identify features (e.g., one or more genes 140) that have the largest contribution or influence on the deep learning architecture 130 output or prediction. The primary goal of the XAI 135 is to define an importance measure (e.g., Shapley values) that identifies which gene(s) play an important role in the determination of a phenotype. XAI refers to techniques in the application of artificial intelligence (AI) such that the decisions (e.g., the solution results) of a machine learning model can be understood and interpreted. XAI contrasts with the concept of the "black box" in machine learning where even the designers of a machine learning model cannot explain why the AI arrived at a specific decision by the machine learning model. In some instances, the technique used for XAI 135 is SHapley Additive exPlanations (SHAP), which is a game theoretic approach to analyze and explain the decisions of a machine learning model. However, it will be appreciated that other techniques for XAI are contemplated to understand and interpret predictions made by machine learning models. For example, alternatively or additionally, gradient based approaches such as integrated gradients, back propagation approaches such as DeepLIFT, model agnostic techniques such as Local Interpretable Model-agnostic Explanations (LIME), neural network and attention weight approaches such as Attention-Based Neural Network Models, or Deep Taylor Decomposition approaches such as Layer-wise Relevance Propagation (LRP) may be used to understand and interpret predictions made by machine learning models.

The core idea behind SHAP-based explanations of machine learning models is to use fair allocation results from cooperative game theory to allocate credit for a model's output among its input features. In other words, the SHAP explanation method breaks down a prediction to show the impact of each feature (e.g., each gene in a gene expression profile). In order to do this, the SHAP explanation method computes Shapley values from cooperative game theory. Features contribute to the model's output or prediction with different magnitude and sign, which is accounted for by the Shapley values. Accordingly, Shapley values represent estimates of each feature's importance (magnitude of the contribution or influence) as well as the direction (sign). Features with positive Shapley values increase the prediction value of the phenotype, whereas features with negative Shapley values decrease the prediction value of the phenotype. The averages of absolute Shapley values may then be used to rank and sort the importance of each feature.

The techniques used for XAI 135 (e.g., SHAP) generate: (i) a set of feature importance scores (quantitative value) for the features used in the prediction (some or all input features), and (ii) a ranking or otherwise sorting of the features through aggregation of the importance scores for each feature for all predictions in a holdout data set or a new set of input data (i.e., a set of gene expression profiles 120). For example, with respect to SHAP, once ranked and sorted by the average of absolute Shapley values, the highest ranking or sorted feature(s) 140 (e.g., set of genes) are identified as having the largest contribution or influence on the deep learning architecture 130 output or prediction. The highest ranking or sorted feature(s) 140 may be identified by sorting and identifying the feature(s) (e.g., a single gene, five genes, ten genes, fifteen genes, or the like) with the largest average of absolute Shapley values. The highest ranking or sorted feature(s) 140 may be the candidate genes to be involved in the molecular regulatory processes for that particular plant species and phenotype, and are used in the second component 110 for modeling gene edits.

Figure 2B:
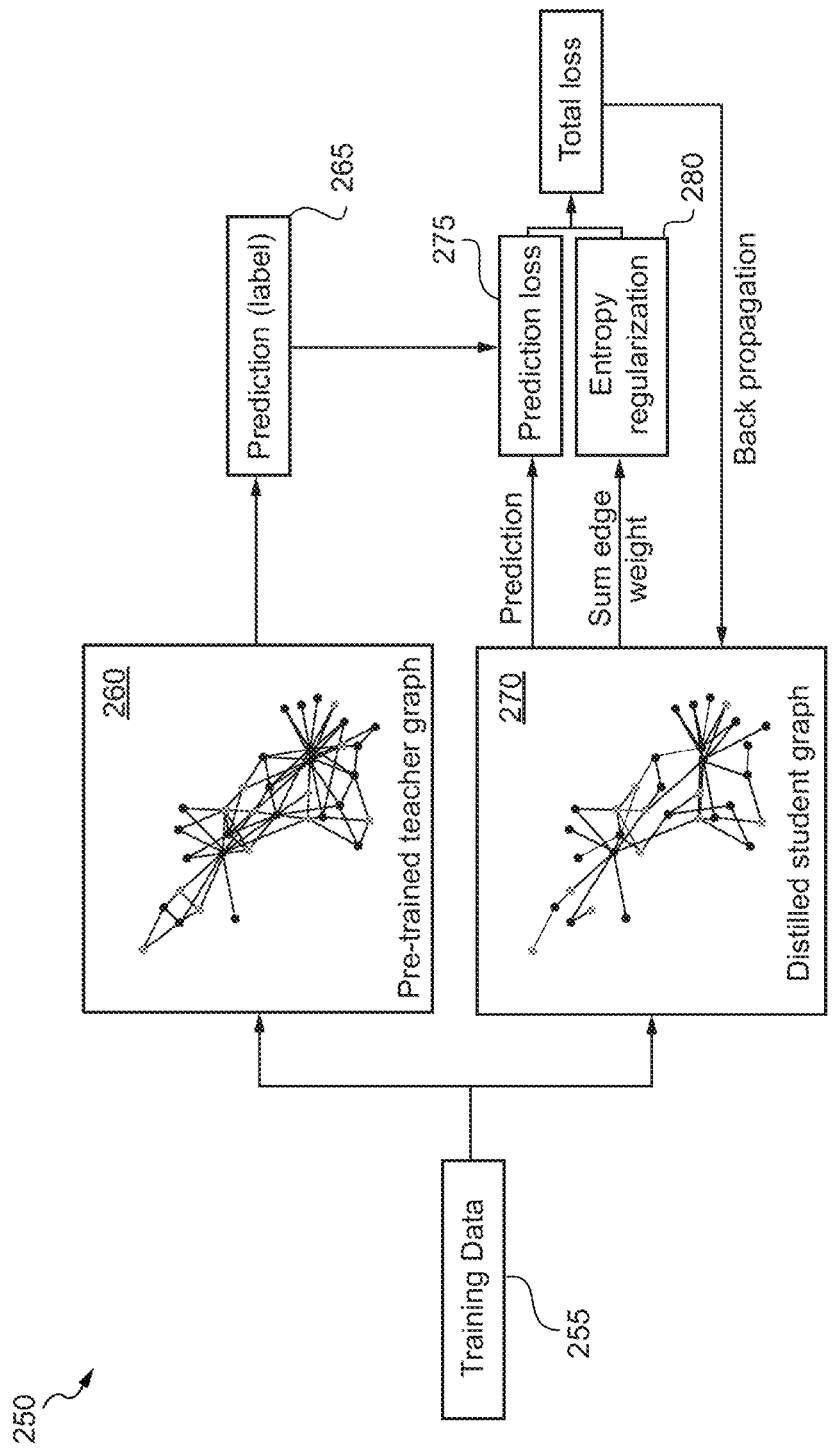
FIG. 2B shows a graph distillation for gene-gene interaction discovery in accordance with various embodiments.

As another example with respect to a GNN, a GNN distillation process may be leveraged to obtain interpretations of the predictions of the GNN by: (i) identifying critical subgraph structures and node features, and (ii) obtaining a subset of important subgraphs for each prediction, whose nodes can be aggregated across samples and ranked to create a list of importance of individual nodes. FIG. 2B shows a graph distillation 250 for gene-gene interaction discovery. The multi-omics training data are transformed into a set of graphs, where each node in the graph represents a gene. The input training data 255 are fed into a frozen pre-trained teacher graph 260 to produce the predictions, which are used as the target labels 265 for the distilled student graph 270. The student graph 270 is trained with two objectives: (1) to make predictions 275 similar to the outputs of the teacher graph 260, and (2) to have a minimum number of edges, achieved through the entropy regularization 280. After the training, the remaining edges in the distilled student graph 270 represent the most important gene-gene interactions that contribute to the given output prediction.

The ranked features 140 (e.g., genes) obtained from the XAI mechanisms on the deep learning architecture 130 serve as the basis for the first component 105. In some instances, sets of features such as genes that are documented in the literature to be associated with a given phenotype can be leveraged to benchmark the performance of the first component 105. For example, given a set of ranked features 140 from the first component 105, a "recall at k" metric can be computed, by computing the number of total literature features captured in the top k features in the ranking of features 140. While k is a critical parameter that can influence this metric, an aggregate metric can be obtained by generating a curve from computing the recall at k, for all k starting from 1 to the number of features in the dataset. Integration of such a curve up to a predetermined number of features, k, yields a continuous value, the "Area Under the Curve to k," that can be used as a metric of accuracy for the first component 105. While the aforementioned approach for benchmarking feature recall is useful to gauge how a model is capturing associations between feature such as genes and phenotypes that have resulted from decades of biological experimentation and validation, the set of true associations is incomplete and thus associations that come from the first component 105 not captured in the known set of literature genes may be correct (confirmed from further biological validation). In some instances, deployment of a trained model for predicting phenotypes and feature discovery can be implemented based on the performance of the model as determined by the approach for benchmarking feature recall. For example, if one model is out performing another model according to the approach for benchmarking feature recall then the higher performing model may be used in deployment for phenotype prediction and feature discovery (e.g., gene discovery).

The second component 110 comprises a model architecture configured to model gene edits and generate ideal gene expression profiles 145 for a given phenotype 115. The model architecture comprises a modeler 150 that uses one or more various approaches (A)-(N) for generating the ideal gene expression profiles 145. The ideal gene expression profiles 145 are a recommendation of gene expression for all genes in the features 140 for maximizing or minimizing the phenotype 115. The ideal gene expression profiles 145 may then be compared to a naturally occurring distribution of gene expression for the plant species to understand whether the gene edit recommendation 155 is to upregulate or downregulate a particular gene, a sub group of genes, or each gene within the ideal gene expression profiles 145.

A first approach (A) comprises modeler 150 ascertaining directionality of regulation (upregulation or downregulation) for modeling gene editing directly from the set of feature importance scores (e.g., Shapley values) for the features 140 used in the prediction. For example, the XAI mechanisms on the deep learning architecture 130 plot the set of feature importance scores (e.g., Shapley values) against the gene expression values (e.g., a binary: 1=expressed or a 0=not expressed) to obtain a correlation between the feature contributions and the predicted phenotype. This correlation is leveraged by the modeler 150 to determine how certain features such as genes can impact the phenotype through upregulation or downregulation in the context of the deep learning architecture 130. For example, the upregulation of gene (a) expression may positively correlate to the predicted phenotype (I); whereas the upregulation of gene (b) expression may negatively correlate to the predicted phenotype (I). The modeler 150 then generates ideal gene expression profiles 145 for a given phenotype 115 based on the ascertained directionality of regulation (upregulation or downregulation). Continuing with the above example, the ideal gene expression profile 145 for phenotype (I) may include the upregulation of gene (a) (or increased expression of gene (a)) and downregulation of gene (b) (or decreased expression of gene (b)) in order to positively contribute expression of the given phenotype (I) within a plant.

A second approach (B) comprises modeler 150 treating the modeling of gene edits as a gene expression optimization problem. More specifically, Bayesian optimization may be used to model the gene edits. Bayesian optimization is a sequential search framework that incorporates both exploration and exploitation to direct the search in order to find the minimum or maximum of an objective function. The goal of Bayesian optimization is to build a probabilistic model of an underlying function that will determine (i) that a given data point is a good place to sample because the function will return a high value (correlation high with given phenotype), and (ii) that another given data point is a good place to sample because uncertainty of return is very large, corresponding to a high amount of knowledge to be gained after the sampling. The Bayesian optimization algorithm comprises two components: (i) a probabilistic model of the underlying function, and (ii) an acquisition function for sampling various data points.

As shown in FIGS. 3A and 3B, the probabilistic model may be a Gaussian process model (as described with respect to deep learning architecture 130) and the underlying function may be a Gaussian process function 305 at the features 310 (e.g., features 140 described with respect to FIG. 1). Using the Gaussian process function 305, the modeler 150 can estimate the distribution of the Gaussian process function 305 at the features 310, which can then be used to direct future sampling. The best estimate of the Gaussian process function 305 is given by the mean $\mu[x]$, and the uncertainty is given by the variance $\sigma^2[x]$. From the Gaussian process function 305 and its uncertainty, the modeler 150 can choose which point to sample next using the acquisition function 315. Sampling involves use of a posterior, which is everything known about the Gaussian process function 305, in the acquisition function 315 for acquiring more samples. In other words, everything known about the Gaussian process function 305 is used to sample the area of the search space that is most likely to pay off, therefore the acquisition function 315 will optimize the conditional probability of locations in the search to generate the next sample. The acquisition function 315 takes the mean and variance at each data point x on the Gaussian process function and computes a value that indicates how desirable it is to sample next at this position (with consideration of exploration and exploitation). In some instances, the acquisition function 315 is a tunable hyperparameter of the model to balance between exploitation and exploration trade-off. Examples of an acquisition function 315 include upper confidence bound, Thompson sampling, expected improvement, and probability of improvement. Once additional samples and their evaluation via the Gaussian process function 305 have been collected, the samples are added to a data set and the posterior is then updated. This process is repeated until the extrema of the Gaussian process function 305 is located, a good enough result is located, or resources are exhausted. Once the iterative process is complete, the modeler 150 generates ideal gene expression profiles 145 for a given phenotype 115 based on the determined extrema of the Gaussian process function 305.

FIG. 3C shows that recommendations by Bayesian optimization are consistent with Shapely values. The top 350 illustrates recommendations by the Bayesian optimization (dashed vertical lines) to sample the next data points to maximize the trait. The bottom 355 illustrates correlations of each gene's expression level with its SHAP values—the higher the SHAP, the more it contributes to the trait. The correlations show that to maximize the trait or phenotype, the first three genes should be downregulated and the last gene should be upregulated, which is consistent with the recommendations provided by the Bayesian optimization on the top 350.

Figure 4:
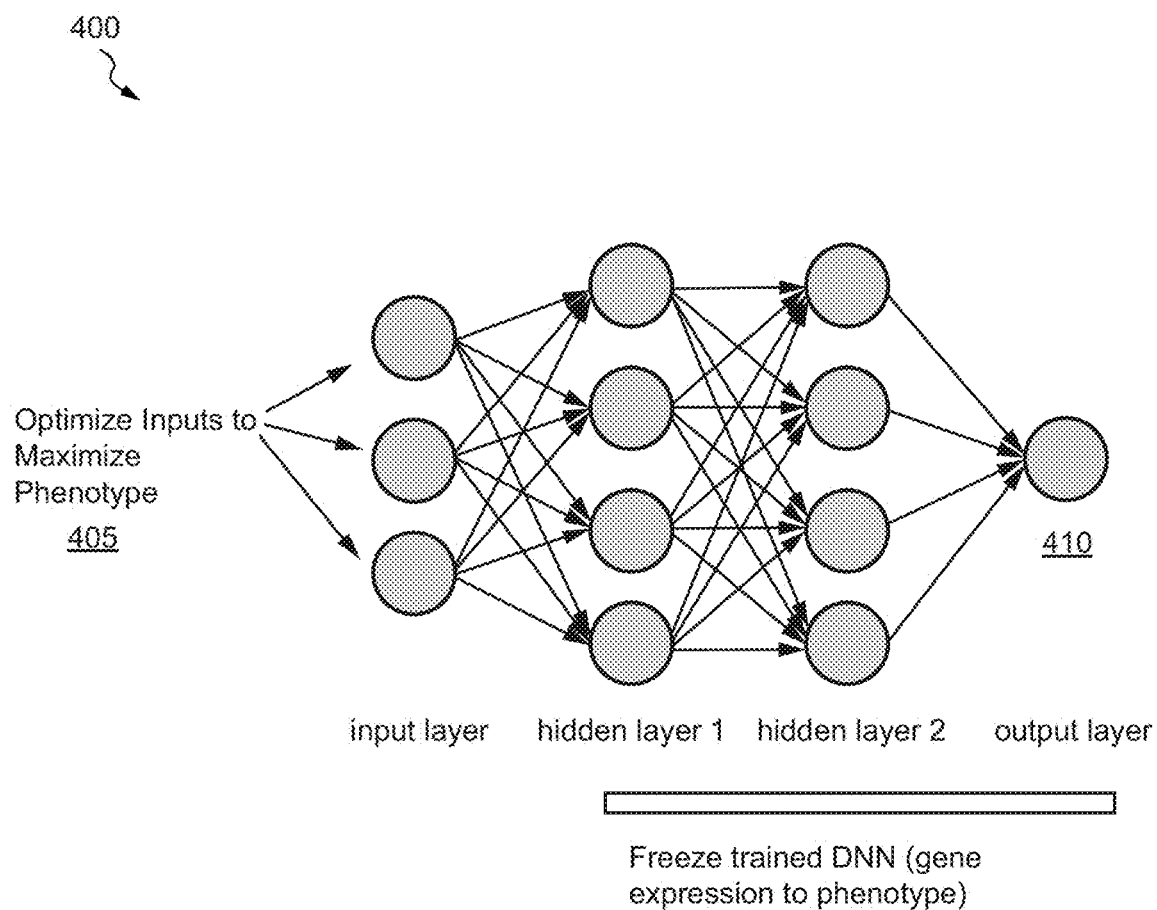
FIG. 4 shows adversarial attack on a deep learning architecture to model gene edits in accordance with various embodiments.

A third approach (C) comprises modeler 150 performing adversarial attack on the deep learning architecture 130 using adversarial examples to model the gene edits. Adversarial examples are inputs to a neural network that result in an altered output from the network. As shown in FIG. 4, performing the adversarial attack comprises inverting the optimization problem by freezing the weights of the trained network 400, and instead optimizing over a set of inputs 405 (adversarial examples) to maximize or minimize the phenotype 410. The optimizing includes: (i) identifying the features 140 described with respect to FIG. 1 such as genes that are in line with the gene discovery component of the pipeline (i.e., the first component 105), (ii) defining a new optimization problem for the trained network 400 as the optimal expression and/or counts of each of the features 140 such as the genes to maximize the phenotype 410 while holding all other gene expressions and/or counts (this could be the mean gene expression and/or counts across all samples), and (iii) define constraints for gene expression based on max/min expression and/or counts observed in the features 140, biologically grounded constraints (e.g., gene (a) and gene (b) express a protein and ligand, respectively, that must be expressed together for binding by the protein), experimental method limitations (e.g., CRISPR/Cas9 have a constraint on the number of genes that can be simultaneously targeted), or any combination thereof.

Figure 5:
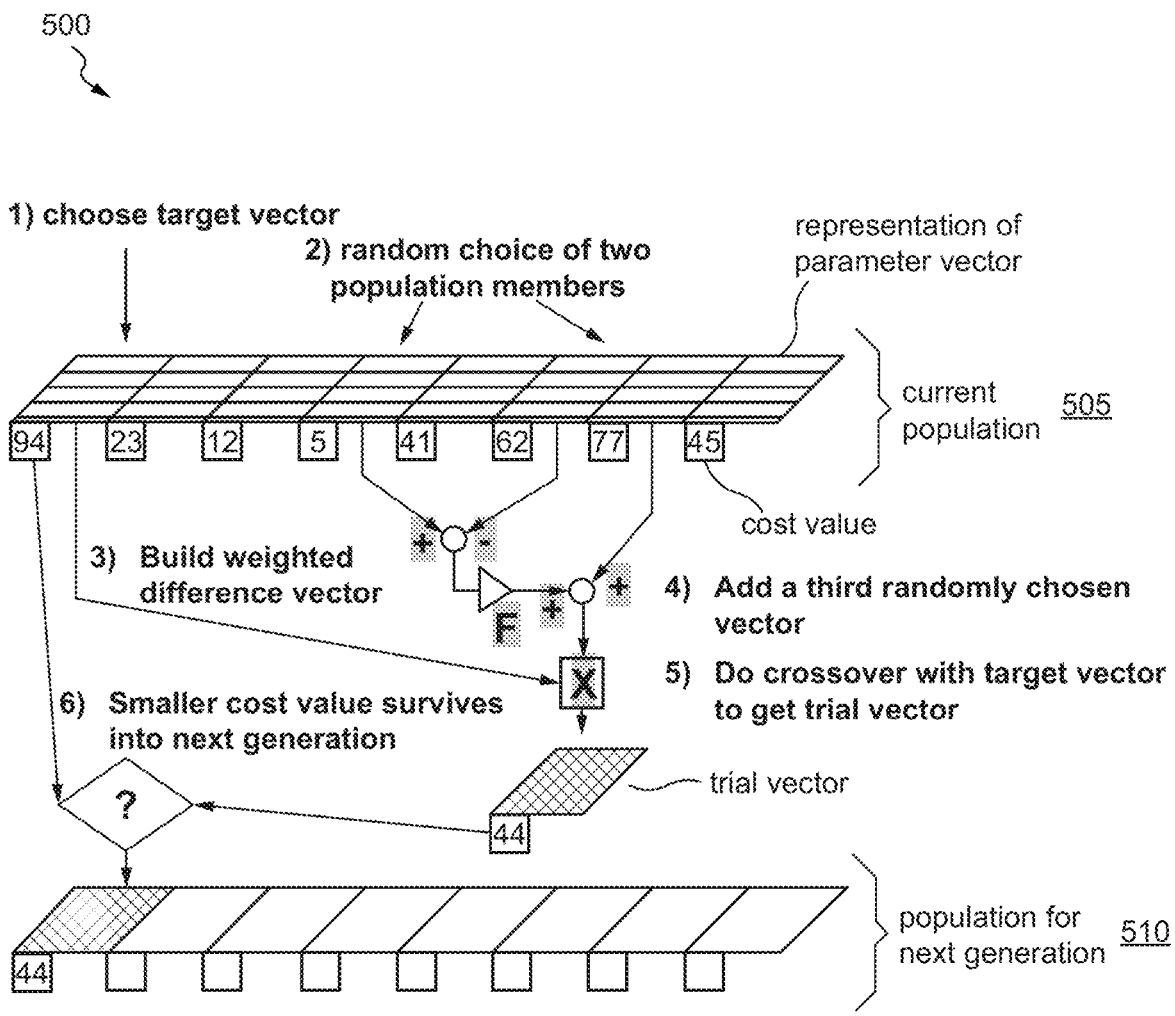
FIG. 5 shows an exemplary differential evolution algorithm in accordance with various embodiments.

In some instances, a gradient based optimization technique is leveraged by the modeler 150 for finding the solution to the defined new optimization problem, which takes the gradient with respect to the set of inputs rather than the weights of the network. In other instances, however, given that it would be advantageous to define constraints for gene expression, discrete optimization techniques such as differential evolution are leveraged by the modeler 150. Differential evolution is a technique that optimizes the problem by iteratively trying to improve a candidate solution (e.g., expression and/or counts of each of the features 140) with regard to a given measure of quality (e.g., a max/min of phenotype 115). As shown in FIG. 5, the differential evolution algorithm 500 searches the design space by maintaining a population of candidate solutions 505 (individuals) and creating new solutions by combining existing ones according to a specific process. In some instances, the specific process includes (i) choosing a target vector, (ii) randomly choosing two population members, (iii) building a weighted difference vector based on the two population members, (iv) adding a third randomly chosen vector for a population member, (v) performing crossover between the weighted difference vector, the third random vector, and the target vector to obtain a trial vector comprising candidates with new objective values (e.g., cost value), and (vi) the candidates with the best new objective values are kept in the next iteration of the algorithm in a manner that the new objective value of an individual is improved forming consequently part of the population for the next generation 510, otherwise the new objective value is discarded. The process repeats itself until a given termination criterion is satisfied. Once the iterative process is complete, the modeler 150 generates ideal gene expression profiles 145 for a given phenotype 115 based on the optimal set of inputs (corresponding to gene expressions) determined from the adversarial attack.

FIG. 6 shows an example of an ideal gene expression profile 600 determined using an adversarial based modeling approach for genes AT2G45660, AT2G45660, AT5G44590, AT3G52480 identified with SHAP based XAI of a DNN. The ideal gene expression profile 600 is shown in comparison to an ideal gene expression profile 605 determined using an adversarial based modeling approach for genes AT2G45660, AT2G45660, AT5G44590, AT3G52480 identified with SHAP based XAI of a linear regression (LR) model. Also shown, is a comparison of the deal gene expression profiles 600/605 to a naturally occurring distribution of gene expression for the plant species over Samples 1-3 to understand whether the gene edit recommendation is to upregulate or downregulate a particular gene, a sub group of genes, or each gene within the ideal gene expression profiles 600/605. In this instance, the recommendation is upregulating AT5G44590 while downregulating AT2G45660, AT2G45660, and AT3G52480 based on the comparison.

As should be understood, other modeling approaches are contemplated and may be implemented. For example, an artificial neural network (ANN) may be trained for gene edit prediction and a gene expression profile may be optimized using the trained ANN. Moreover, although the modeling approaches described herein focus using a single approach for modeling gene edits, two or more of these approaches could be used in combination as an ensemble of approaches and the resulting gene expression profiles could be selected or combined to obtain the ideal gene expression profile. For example, every model makes a prediction (votes) for each test instance and the final output prediction is the one that receives more than half of the votes. If none of the predictions get more than half of the votes, then it may be determined that the ensemble method could not make a stable prediction for the given instance. Alternatively, an averaging technique could be used, where for every instance of the test dataset, the average predictions are calculated. Weights could also be implemented in either of these ensemble techniques to increase the importance of one or more models.

III. Gene Discovery and Editing System

Figure 7:
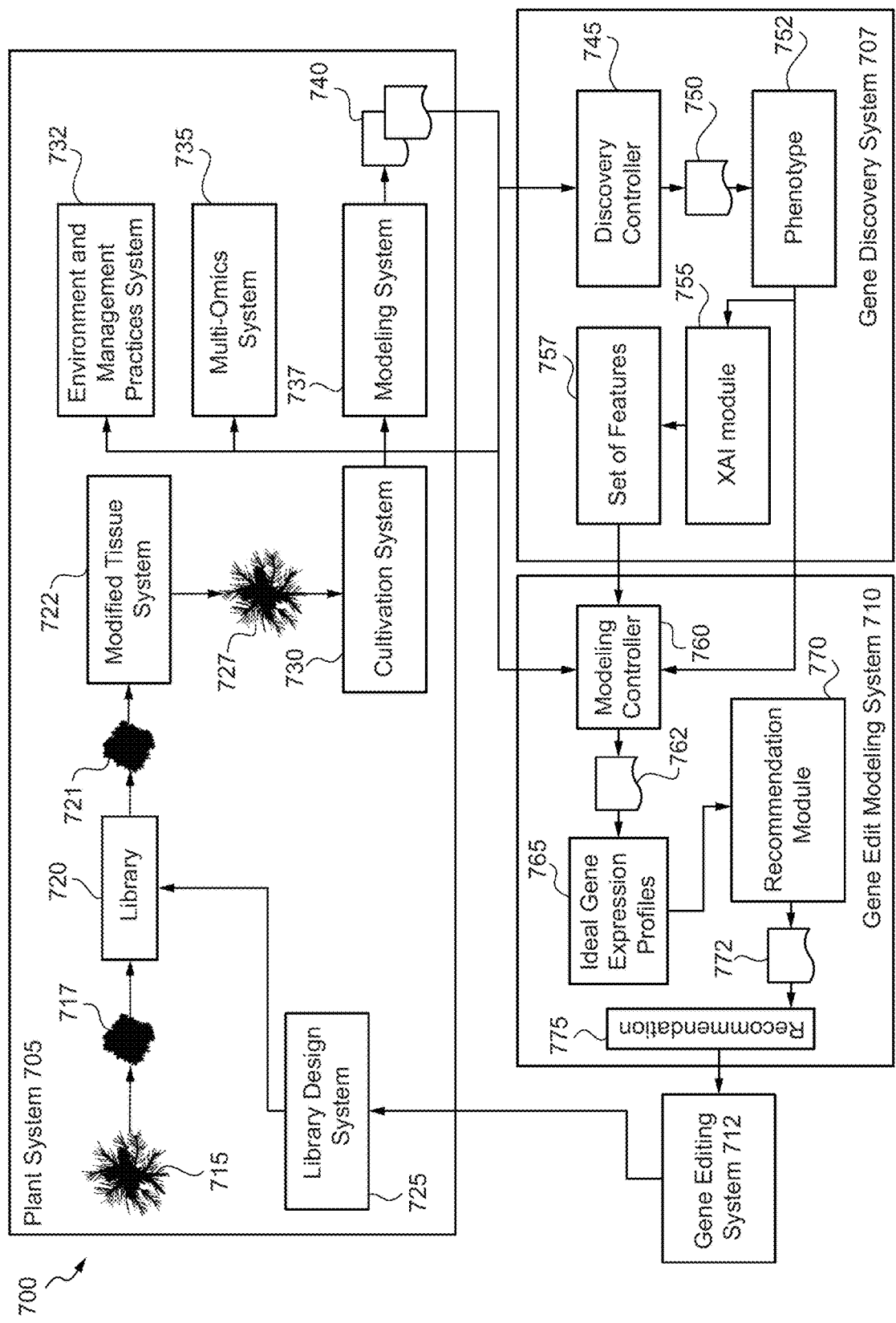
FIG. 7 shows a block diagram of a gene discovery and editing system in accordance with various embodiments.

FIG. 7 shows a block diagram of gene discovery and editing system 700. The gene discovery and editing system 700 is an example of a system implemented as computer programs on one or more computing devices in one or more locations in which the systems, components, and techniques described herein are implemented. The gene discovery and editing system 700 includes a plant system 705, a gene discovery system 707, a gene edit modeling system 710, and a gene editing system 712.

The plant system 705 can execute a plant generation lifecycle by starting with a plant 715. The plant 715 can be dissected, either by an automated system, e.g., a robotic control system, or manually, to obtain plant tissue 717. The plant tissue 715 can then be modified using a library 720 to generate modified tissue 721. The library 720 is a collection of multiple versions of reagents, for example a collection of DNA sequences combinatorially assembled to give many different versions of a metabolic pathway. The library 720 can, for example, include plasmids, linear DNA fragments, synthetic guide RNAs (sgRNAs), RNAs, proteins, etc. The library 720 can be generated from a library design system 725 that compiles information for the library 720 from either output generated from a model during a previous lifecycle of a plant, or from another source, for example, manual design from experts.

A modified tissues system 722 grows e.g., in a culture, the modified tissue 721 into a new plant 727, and provides the new plant 727 to a cultivation system 730. The cultivation system 730 may be governed by an environment and management practices system 732 that dictates the environmental conditions and the management practices under which the plants 727 are grown. The cultivation system 730 obtains tissue samples and measurements from the plants 727 as they grow, extracts data from the samples and measurements, and provides the extracted data to the environment and management practices system 732, the multi-omics system 735, and/or the modeling system 737. The data extraction can include tissue sampling, molecule extraction and purification, and molecule quantification or identification, and can occur in any or a multitude of separate tissues/organs of the plant at various times of growth or continuously though-out the life cycle of plant 727. The environment and management practices system 732 provides the extracted data (if received from the cultivation system 730), management practice profile data, and environment conditions profile data to the modeling system 737 for development of various models 740. The management practices profile data may include any adjustable aspect of the management of the growth of the plant 727 at various times of growth or continuously though-out the life cycle of plant 727, e.g., inputs such as fertilizer or water, the timing of planting, fertilizing, harvesting, etc. The data environment conditions profile data may include the location-specific environmental conditions of the plant 727 is exposed to at various times of growth or continuously though-out the life cycle of plant 727, e.g. temperature, precipitation, soil properties, etc. The multi-omics system 735 tracks the extracted data from the samples and measurements, generates multi-omics profiles (e.g., a gene expression profiles) of the small plant from the extracted data, and provides the multi-omics profiles to the modeling system 737 for development of the various models 740.

The modeling system 737 uses the received data (e.g., plant extracted data, multi-omics profiles, management practices profiles, environmental conditions profiles, etc.) for the development (e.g., design, training, validation, and deployment) of various models (e.g., machine learning models) that the gene discovery and editing system 700 can then use to guide growth of present plants 727 and the generation of new plants with desired phenotypes. For example, the modeling system 737 can provide the trained or updated machine learning models to (i) the library designs system 725 to guide the modification of new plants, (ii) the environment and management practice system 732 to guide the growth and management of the plants 727, (iii) the gene discovery system 707 to generate phenotype predictions and facilitate gene discovery, and (iv) the gene edit modeling system 710 to model gene edits, generate ideal gene expression profiles, and facilitate the recommendation of gene edits.

The gene discovery system 707 includes a discovery controller 745 for obtaining input data (e.g., plant extracted data, multi-omics profiles such as gene expression profiles from multi-omics system 735, management practices profiles from management practice system 732, environmental conditions profiles) for one or more plants (e.g., plants 727 being grown in the plant system 705) and inputting the data into one or more models 750. The input data can be obtained from the environment and management practices system 732, the cultivation system 730, the multi-omics system 732, and/or the modeling system 737. The one or more models 750 (e.g., the deep learning architecture 130 described with respect to FIG. 1) are constructed for the task of predicting a phenotype 752 as the output data by learning relationships or correlations between features of the input data (e.g., gene expression profiles within the multi-omics profiles) and the phenotype. The one or more models 750 may be obtained from the modeling system 737 (various models 740). The gene discovery system 707 further includes an XAI module 755 for applying explainable techniques to the one or more models 750 to obtain the importance of each feature for all predictions in a set of input data (e.g., a set of gene expression profiles). In some instances, the one or more models 750, which predicts the phenotype 752, using gene expression profiles as inputs is inspected via XAI module 755 to identify features (e.g., one or more genes) that have the largest contribution or influence on the one or more models 750 output or prediction. The primary goal of the XAI module 755 is to define an importance measure (e.g., Shapley values) that identifies which features, such as gene(s), play an important role in the determination of a phenotype. The XAI module 755 outputs a set of features 757 that may be the candidate genes to be involved in the molecular regulatory processes for that particular plant species and phenotype, and are used in by the gene edit modeling system 710 for modeling gene edits.

The gene edit modeling system 710 includes a modeling controller 760 for obtaining the phenotype 752 and the set of features 757, and inputting the phenotype 752 and the set of feature(s) 757 into one or more models 762. The one or more models 762 may be obtained from the modeling system 737 (various models 740). The one or more models 762 (e.g., modeler 150 described with respect to FIG. 1) use one or more various approaches (A)-(N) for modeling gene edits and generating ideal gene expression profiles 765. The ideal gene expression profiles 765 are a recommendation of gene expression for all genes in the set of features 757 for maximizing, minimizing, or otherwise modulating the phenotype 752. The gene edit modeling system 710 further includes a recommendation module 770 for comparing the ideal gene expression profiles 765 to a naturally occurring distribution of gene expression for the plant species (e.g., gene expressions within the multi-omics profiles) to determine a gene edit recommendation 775 that can be used by the gene editing system 712. The recommendation 775 may be for upregulating or downregulating a particular gene, a sub group of genes, or each gene within the ideal gene expression profiles 765. In some instances, the recommendation module 770 uses one or more models 772 for determining where to make edits that will modulate the expression of genes based on the ideal gene expression profiles 765. These can be regions of multiple base pairs, potentially with strategies on how to make combinatorial edits to those regions, or exact locations with specific edits determined.

The one or more models 772 may be a neural network or nonlinear model that predicts a target gene's expression level from a target gene's genomic context gathered from a genetically diverse plant population. The one or more models 772 may be trained on any of the following population data given the target gene's context: genomic sequence, SNPs, methylome, chromatin accessibility, and the like in combination with corresponding expression values. Recommendations for genomic edits may be extracted from the target gene's expression level following investigation of feature importance along with input feature ablation analysis of the one or more models 772.

The gene editing system 712 makes genetic edits or perturbations to the genome of a given plant species (e.g., plant 727) in accordance with the recommendation 775. Examples of gene editing systems include CRISPR/Cas9, CRISPR/Cpf1, CRISPR/Cas12, CRISPR base editing, CRISPR inhibition, restriction enzymes, Zinc Finger Nucleases, Transcription activator-like effector nucleases (TALEN), and the like. For example, gene editing system 712 may make one or more combinatorial edits ("bashing") in the gene regulatory genomic regions (promoters, 5'UTR, 3'UTR, terminator) of one or more target genes in order to modify their expression (upregulation or downregulation). Additionally or alternatively, gene editing system 712 may make one or more specific combinatorial edits to the binding site of a transcription factor of one or more target genes in order to modulate their effect on expression (upregulation or downregulation). Additionally or alternatively, gene editing system 712 may make one or more genomic modifications of any other region on the genome that may affect one or more target gene's expression (upregulation or downregulation) via genetic manipulation. Additionally or alternatively, gene editing system 712 may modulate the expression (upregulation or downregulation) of one or more target genes without genomic modifications, such as CRISPRi (target inhibition), CRISPRa (target activation), RNAi, etc. The system could also make crosses if the edits determined by system 710 are already accessible in the population. The modified genome of the given plant species may then be sent to the library design system 725 for use by the library 720 and the modified tissues system 722 to grow e.g., in a culture, modified tissues from the modified genome into a new plant.

IV. Gene Discovery and Editing Techniques

Figure 8:
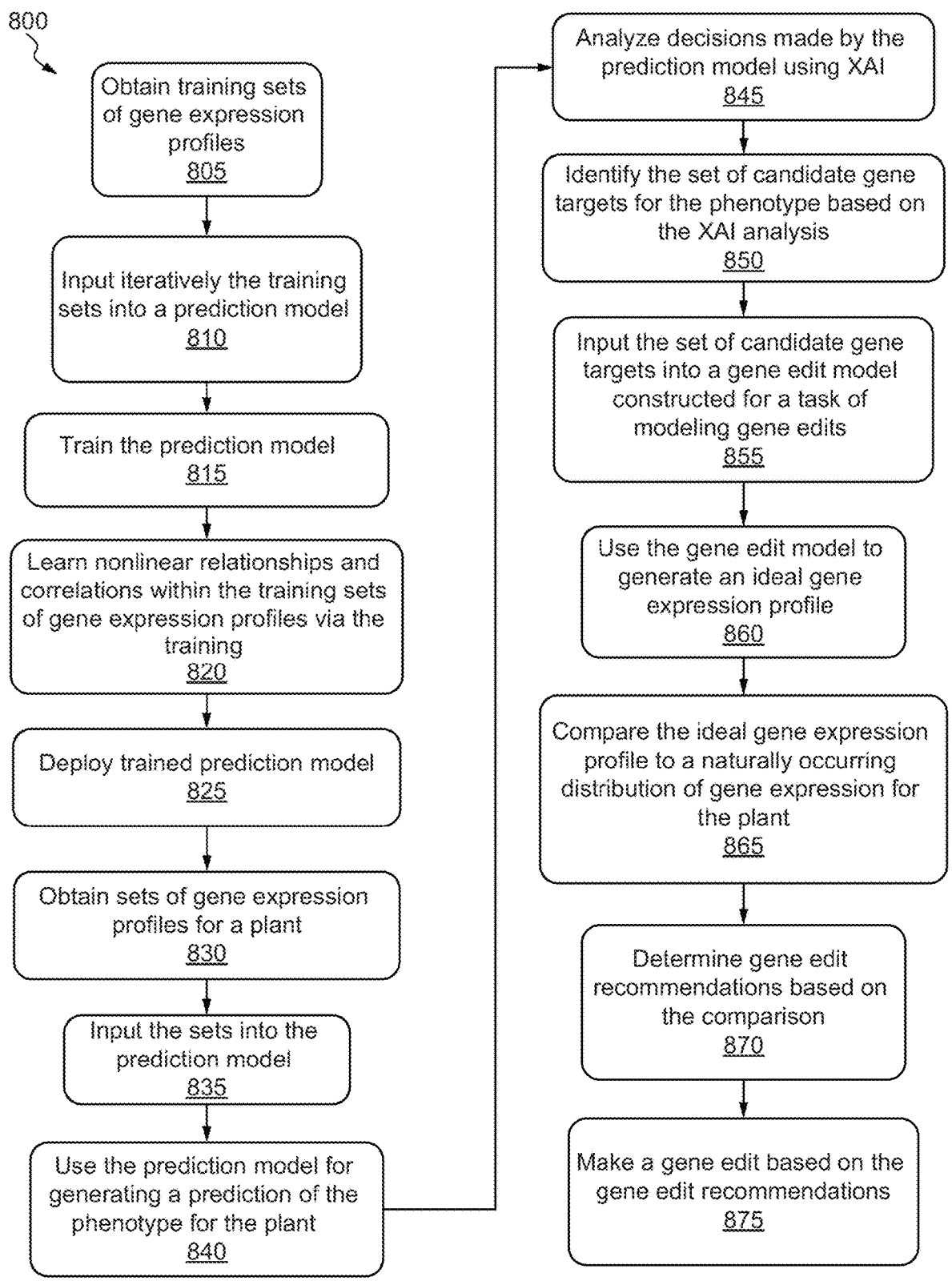
FIG. 8 shows an exemplary flow for gene discovery and editing in accordance with various embodiments.

FIG. 8 is a simplified flowchart 800 illustrating an example of processing for gene discovery and editing. The processing depicted in FIG. 8 may be implemented in software (e.g., code, instructions, program) executed by one or more processing units (e.g., processors, cores) of the respective systems, hardware, or combinations thereof. The software may be stored on a non-transitory storage medium (e.g., on a memory device). The method presented in FIG. 8 and described below is intended to be illustrative and non-limiting. Although FIG. 8 depicts the various processing steps occurring in a particular sequence or order, this is not intended to be limiting. In certain alternative embodiments, the steps may be performed in some different order or some steps may also be performed in parallel. In some embodiments, such as in the embodiments depicted in FIGS. 1 and 7, the processing depicted in FIG. 8 may be performed by components of the machine learning pipeline 100 and/or gene discovery and editing system 700 described with respect to FIGS. 1 and 7.

Process 800 begins at block 805 where training sets of gene expression profiles are obtained for a set of genes measured in a tissue sample(s) of a plant. At block 810, training sets of gene expression profiles are iteratively input into a prediction model constructed for a task of predicting a phenotype as output data by a nonlinear algorithm learning relationships or correlations between features of gene expression profiles and the phenotype. At block 815, the prediction model is trained on the training sets of gene expression profiles by minimizing a loss or error function. In some embodiments, the prediction model is a deep neural network such as a feedforward neural network. In other embodiments, the prediction model is another type of nonlinear model such as a Gaussian process model. Each iteration of the training process for the prediction model can involve inputting data sets from the training and/or tuning set and learning a set of model parameters (configured with a defined set of hyperparameters) so that the value of the loss or error function (e.g., modified cross entropy loss) using the set of model parameters is smaller than the value of the loss or error function using a different set of model parameters in a previous iteration. The loss or error function can be constructed to measure the difference between the labels/ground truth and the inferred data such as an inferred phenotype for the training sets of gene expression profiles.

At block 820, in response to the training, the nonlinear algorithm learns the relationships and correlations within the training sets of gene expression profiles that are used to predict a phenotype of the plant. Additionally, in response to the training, a learned set of model parameters associated with the relationships or correlations between features of gene expression profiles and the phenotype is obtained for the prediction model. At block 825, the trained prediction model is deployed as a prediction model with the learned set of model parameters.

At block 830, a set of gene expression profiles is obtained for a set of genes measured in a tissue of a plant. At block 835, the set of gene expression profiles are input into the prediction model constructed for a task of predicting a phenotype as output data. At block 840, the prediction model is used for generating a prediction of the phenotype for the plant based on the relationships or the correlations between the features of the set of gene expression profiles and the phenotype. At block 845, decisions made by the prediction model to predict the phenotype are analyzed by an explainable artificial intelligence system, The analyzing comprises: (i) generating a set of feature importance scores for the features used in the prediction of the phenotype, and (ii) ranking or otherwise sorting the features based on the feature importance score associate with each of the features. The explainable artificial intelligence system may use SHAP, integrated gradients, LIME, Attention-Based Neural Network Models, or LRP to analyze the decisions made by the prediction model. At block 850, the set of candidate gene targets for the phenotype as having a largest contribution or influence on the prediction are identified based on the ranked features, For example, the top one, five, ten, fifteen, or the like genes having a largest contribution or influence on the prediction are identified as candidate gene targets based on the ranked features.

At block 855, a set of genomic regions are identified, based on the identified set of candidate gene targets, that when edited provide a requisite change in a gene expression profile to realize an expected phenotypic change. The identifying the set of genomic regions comprises inputting the set of candidate gene targets into a gene edit model constructed for a task of modeling gene edits of the set of candidate gene targets, and identifying, based on the modeled gene edits, an optimal set of genetic targets for genome editing each gene within the set of candidate gene targets, thus maximizing, minimizing, or otherwise modulating the phenotype. At block 860, the gene edit model is used to generate an ideal gene expression profile for the phenotype based on the optimal set of genetic targets for the genome editing each gene within the set of candidate gene targets. In instances in which the explainable artificial intelligence system uses SHAP, the gene edit model may model the gene edits by ascertaining directionality of regulation directly from the Shapley values. In instances in which the prediction model is a Gaussian process model, the gene edit model may model the gene edits using a Bayesian optimization algorithm comprising two components: (i) the Gaussian process model of an underlying Gaussian process function, and (ii) an acquisition function for sampling various data points. In instances in which the prediction model is a deep neural network, the gene edit model may model the gene edits by performing an adversarial attack on the deep neural network, the adversarial attack comprising freezing the weights of the deep neural network, and optimizing over a space of constrained inputs to maximize, minimize, or otherwise modulate the phenotype.

At block 865, the ideal gene expression profile is compared to a naturally occurring distribution of gene expression for the plant. At block 870, a gene edit recommendation for upregulating or downregulating a particular gene, a sub group of genes, or each gene within the ideal gene expression profiles is determined based on the comparison between the recommended expression profile and the naturally occurring expression profiles across the existing samples. At block 875, the gene editing system is used to make a genetic edit or perturbation to a genome of the plant in accordance with the gene edit recommendation.

Figure 9:
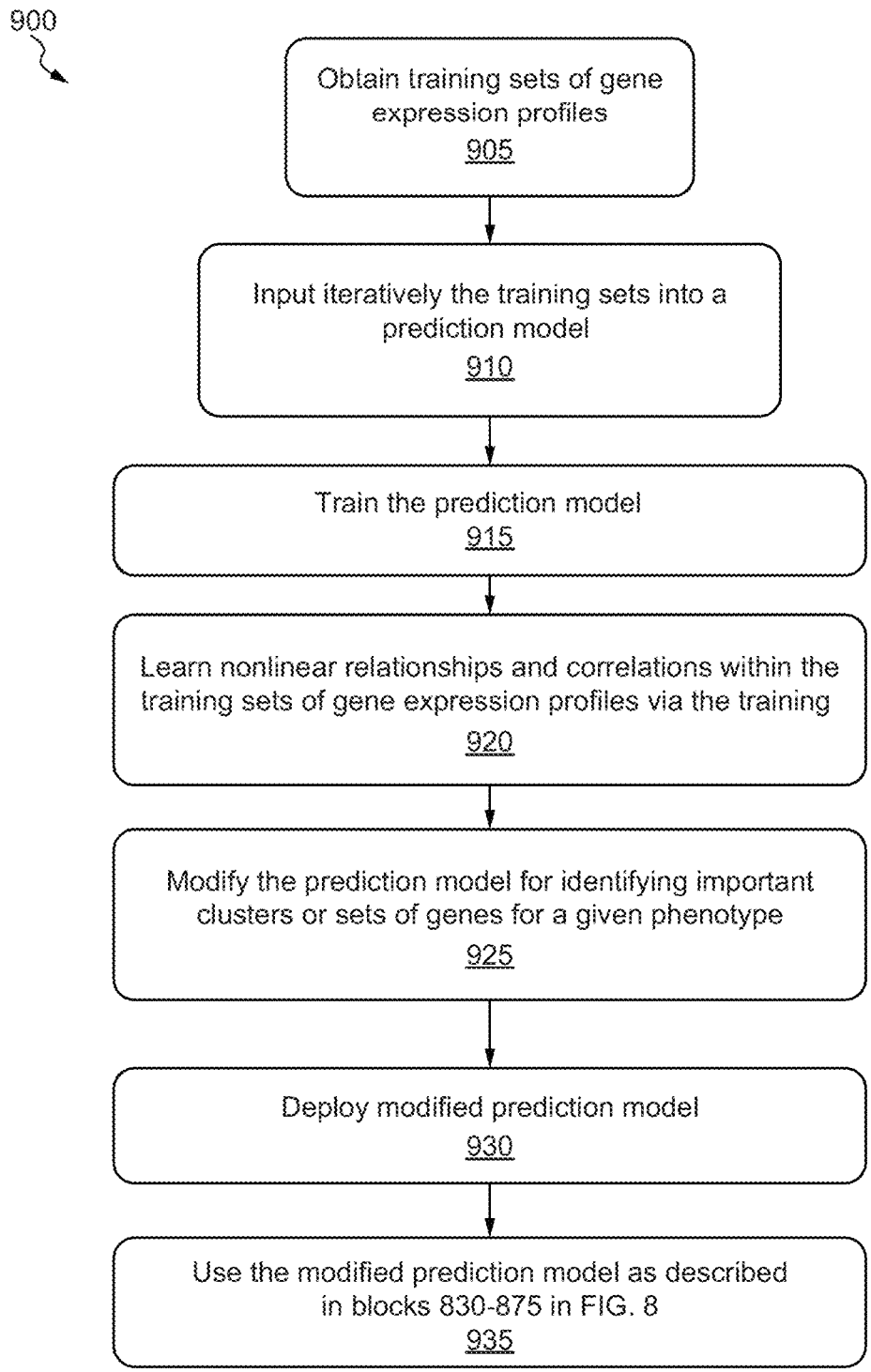
FIG. 9 shows an exemplary flow for identifying important gene sets or clusters for a given phenotype in accordance with various embodiments.

FIG. 9 is a simplified flowchart 900 illustrating an example of processing for identifying important gene sets or clusters for a given phenotype. In this exemplary process sets or clusters of genes that are significant in the prediction of a given phenotype are identified via the interpretation of SHAP/XAI values in the second layer of a deep neural network. However, it should be understood that all the other XAI and modeling techniques described herein (e.g., LIME, integrated gradients, Bayesian optimization, adversarial attack, and the like) can be applied in a similar manner with this clustering technique instead of directly on single gene information. The processing depicted in FIG. 9 may be implemented in software (e.g., code, instructions, program) executed by one or more processing units (e.g., processors, cores) of the respective systems, hardware, or combinations thereof. The software may be stored on a non-transitory storage medium (e.g., on a memory device). The method presented in FIG. 9 and described below is intended to be illustrative and non-limiting. Although FIG. 9 depicts the various processing steps occurring in a particular sequence or order, this is not intended to be limiting. In certain alternative embodiments, the steps may be performed in some different order or some steps may also be performed in parallel. In some embodiments, such as in the embodiments depicted in FIGS. 1 and 7, the processing depicted in FIG. 9 may be performed by components of the machine learning pipeline 100 and/or gene discovery and editing system 700 described with respect to FIGS. 1 and 7.

Process 900 begins at block 905 where training sets of gene expression profiles are obtained for a set of genes measured in a tissue sample(s) of a plant. At block 910, training sets of gene expression profiles are iteratively input into a deep neural network model (e.g., a feed forward neural network model) constructed for a task of predicting a phenotype as output data by a nonlinear algorithm learning relationships or correlations between features of gene expression profiles and the phenotype. At block 915, the deep neural network model is trained on the training sets of gene expression profiles by minimizing a loss or error function. Each iteration of the training process for the deep neural network model can involve inputting data sets from the training and/or tuning set and learning a set of model parameters (configured with a defined set of hyperparameters) so that the value of the loss or error function (e.g., modified cross entropy loss) using the set of model parameters is smaller than the value of the loss or error function using a different set of model parameters in a previous iteration. The loss or error function can be constructed to measure the difference between the labels/ground truth and the inferred data such as an inferred phenotype for the training sets of gene expression profiles.

At block 920, in response to the training, the nonlinear algorithm learns the relationships and correlations within the training sets of gene expression profiles that are used to predict a phenotype of the plant. Additionally, in response to the training, a learned set of model parameters associated with the relationships or correlations between features of gene expression profiles and the phenotype is obtained for the deep neural network model.

At block 925, the trained deep neural network model is modified for identifying important clusters or sets of genes for a given phenotype. In some instances, given the trained deep neural network model with N layers and input dimension D (where D is the number of genes for which expression information has been obtained), the first hidden layer in the deep neural network model may be isolated and the set of weights or model parameters associated with each node of the first hidden layer extracted from the deep neural network model. For each node in the first hidden layer, a cluster relationship is defined with the nodes in the original input layer by taking the top K components (absolute values) of each weight vector, in which K is defined to be an ideal size of the cluster. Since each node in the first hidden layer (prior to the activation step) may be represented by a linear combination of the inputs, this clustering mechanism intuitively makes a map from each node in the first hidden layer to a set of genes that have the strongest influence on the node in the first hidden layer. Alternative clustering beyond top-k can be used to create this mapping, including methods that flexibly define a unique k for every node of a hidden layer based on the distribution of weights corresponding to that specific node, or a separate clustering step on the weights themselves, taking the genes in the top cluster.

Now that a mapping is created between each node in the first hidden layer and its corresponding genes in the input space, the input layer of the deep neural network mode can be removed and XAI such as SHAP or integrated gradients can be used in downstream processing to obtain feature importance scores for the neural network. Since the first hidden layer of the deep neural network now becomes the input layer, a set of feature importance scores is obtained for every single node in the first hidden layer. The set of feature importance scores obtained for every single node in the first hidden layer may be joined with the mapping of nodes in the first hidden layer to the original genes to get a set of feature importance scores for these clusters or sets of genes.

At block 930, the modified deep neural network model is deployed as a deep neural network model with the learned set of model parameters and the mapping of nodes in the first hidden layer to the original genes. At block 935 the modified deep neural network model can be used for gene discovery and editing, as described with respect to blocks 830-870 of FIG. 8.

V. Examples

The systems and methods implemented in various embodiments may be better understood by referring to the following examples.

Example 1: A sequential neural network was built to model the time taken by natural genetic variant lines of *Arabidopsis thaliana* to reach the reproductive stage (time to flower). In one example, the model was trained on publicly available transcriptomes collected from leaves (Kawakatsu et al., 2016, Cell, 166(2):492-505). The transcriptomic data was available for 728 natural genetic variants, 620 of which carried flowering time information (in days initiation of bolting). The transcriptomic data was experimentally generated by RNA-seq, quantile normalized, and subsequently preprocessed by standardizing the original 24,175 transcript counts (features) to unit variance. A hold-out dataset was created prior to model training, which contained 20% of the original data. The remaining 80% of the data was used to train the models. These included (1) a ridge regression model and (2) a multitude of sequential neural networks with hyperparameters tuned by the algorithm in the AutoKeras implementation (Jin et al., 2019, In Proceedings of the 25th ACM SIGKDD International Conference on Knowledge Discovery & Data Mining (pp. 1946-1956)). The highest performing neural network model architecture— measured as the lowest mean-squared-error on a 20% validation dataset—was subsequently cross-validated on the full dataset. Pearson correlation and Spearman rank correlation coefficients were averaged to compare the model's performance on the same hold-out dataset. Feature importance scores obtained after applying SHapley Additive exPlanations were averaged across models trained on different splits of the data, and subsequently rank sorted. The degree by which models identified sets of influential genes was benchmarked against a list of genes known in the scientific literature to be involved in the phenotype of interest. Expression level recommendations, including directionality of proposed changes, of the top influential genes as output from the models, were further confirmed by correlative analysis with the phenotype value. Genome edits to affect the directionality of change in gene expression were proposed based on modeling of regulatory sequences surrounding the target gene's sequence, additionally incorporating chromatin accessibility information such as ChIP-seq and epigenomic marks. Proposed regulatory regions for gene editing, were targeted for genetic modification by combinatorial CRISPR/Cas9 editing in *Arabidopsis*. This process produces large-scale genetic variation in the regulatory regions of the targeted genes in populations of *Arabidopsis*. Further acquisition of molecular and phenotypic data from these populations is expected to iteratively improve the performance of the current suite of models.

VI. Additional Considerations

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium", "storage" or "memory" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:
1. A method comprising:
    obtaining a set of gene expression profiles for a set of genes measured in a tissue sample of a plant;
    inputting the set of gene expression profiles into a prediction model having a deep learning architecture constructed for a task of predicting a phenotype as output data by learning relationships or correlations between features of the set of gene expression profiles and the phenotype;
    generating, using the prediction model, the prediction of the phenotype for the plant based on the relationships or the correlations between the features of the set of gene expression profiles and the phenotype;
    analyzing, by an explainable artificial intelligence system, decisions made by the prediction model to predict the phenotype, wherein the analyzing comprises: (i) generating a set of feature importance scores for the features used in the prediction of the phenotype, wherein the feature importance scores represent estimates of each features contribution or influence on the prediction of the phenotype, and (ii) ranking or otherwise sorting the features based on the feature importance score associated with each of the features, wherein highest ranking or sorted features are identified as having a largest contribution or influence on the prediction of the phenotype;
    identifying, based on the ranked or otherwise sorted features, a set of candidate gene targets for the phenotype as having the largest contribution or influence on the prediction of the phenotype;
    inputting the set of candidate gene targets into a gene edit modeling system having an architecture constructed to model gene edits and generate ideal gene expression profiles for the phenotype using one or more modeling approaches and the set of candidate gene targets, wherein the one or more modeling approaches generate the ideal gene expression profiles based on the feature importance scores, an optimization algorithm, the prediction model, or any combination thereof;
    generating, using the gene edit modeling system, an ideal gene expression profile for the phenotype based on an optimal set of genetic targets for editing of each gene within the set of candidate gene targets, wherein the ideal gene expression profile is a recommendation of gene expression for the set of candidate gene targets for maximizing, minimizing, or otherwise modulating the phenotype; and
    making, using a gene editing system, a genetic edit or perturbation to a genome of the plant based on the optimal set of genetic targets for editing each gene and the ideal gene expression profile.
2. The method of claim 1, wherein the explainable artificial intelligence system uses SHapley Additive explanations, DeepLIFT, integrated gradients, Local Interpretable Model-agnostic Explanations (LIME), Attention-Based

Neural Network Models, or Layer-wise Relevance Propagation to analyze the decisions made by the prediction model.

3. The method of claim 1, wherein the one or more modeling approaches comprises: (i) modeling the gene edits by ascertaining directionality of regulation directly from the feature importance scores, (ii) modeling the gene edits using a Bayesian optimization algorithm, (iii) modeling the gene edits by performing adversarial attack on the prediction model, or (iv) any combination thereof.

4. The method of claim 1, wherein:
the explainable artificial intelligence system uses SHapley Additive explanations, which generates (i) a set of Shapley values as the feature importance scores for the features used in the prediction of the phenotype and (ii) correlations between the features and the phenotype;
the Shapley values represent estimates of each feature's importance as well as a direction; and
the gene edit modeling system models the gene edits by ascertaining directionality of regulation directly from the Shapley values, wherein the gene edit modeling system is configured to determine how candidate gene targets impact the phenotype through upregulation or downregulation based on the correlations.

5. The method of claim 1, wherein:
the prediction model is a Gaussian process model; and
the gene edit modeling system models the gene edits using a Bayesian optimization algorithm comprising two components: (i) the Gaussian process model of an underlying Gaussian process function, and (ii) an acquisition function for sampling various data points, wherein the Bayesian optimization algorithm is built based on a sequential search framework that incorporates both exploration and exploitation to direct a search to find a minimum or maximum of an objective function, and wherein the gene edit modeling system is configured to estimate a distribution of the underlying Gaussian process function at the features used in the prediction of the phenotype and use the distribution to direct the sampling by the acquisition function.

6. The method of claim 1, wherein:
the prediction model is a deep neural network; and
the gene edit modeling system models the gene edits by performing an adversarial attack on the deep neural network, the adversarial attack comprising freezing weights of the deep neural network, and optimizing over a space of constrained inputs to maximize or minimize the phenotype, wherein the optimizing comprises:
identifying the candidate gene targets;
defining an optimization problem for the deep neural network based on an optimal expression corresponding to a set of the candidate gene targets to maximize the phenotype;
defining constraints for gene expression based on the optimal expression; and
generating the optimal set of genetic targets by the adversarial attack.

7. The method of claim 1, further comprising:
comparing the ideal gene expression profile to a naturally occurring distribution of gene expression for the plant; and
determining a gene edit recommendation for upregulating or downregulating a particular gene, a sub group of genes, or each gene within the ideal gene expression profiles based on the comparing.

8. A computer-program product tangibly embodied in a non-transitory machine-readable storage medium, including instructions configured to cause one or more data processors to perform actions including:
obtaining a set of gene expression profiles for a set of genes measured in a tissue sample of a plant;
inputting the set of gene expression profiles into a prediction model having a deep learning architecture constructed for a task of predicting a phenotype as output data by learning relationships or correlations between features of the set of gene expression profiles and the phenotype;
generating, using the prediction model, the prediction of the phenotype for the plant based on the relationships or the correlations between the features of the set of gene expression profiles and the phenotype;
analyzing, by an explainable artificial intelligence system, decisions made by the prediction model to predict the phenotype, wherein the analyzing comprises: (i) generating a set of feature importance scores for the features used in the prediction of the phenotype, wherein the feature importance scores represent estimates of each features contribution or influence on the prediction of the phenotype, and (ii) ranking or otherwise sorting the features based on the feature importance score associated with each of the features, wherein highest ranking or sorted features are identified as having a largest contribution or influence on the prediction of the phenotype;
identifying, based on the ranked or otherwise sorted features, a set of candidate gene targets for the phenotype as having the largest contribution or influence on the prediction of the phenotype;
inputting the set of candidate gene targets into a gene edit modeling system having an architecture constructed to model gene edits and generate ideal gene expression profiles for the phenotype using one or more modeling approaches and the set of candidate gene targets, wherein the one or more modeling approaches generate the ideal gene expression profiles based on the feature importance scores, an optimization algorithm, the prediction model, or any combination thereof;
generating, using the gene edit modeling system, an ideal gene expression profile for the phenotype based on an optimal set of genetic targets for editing of each gene within the set of candidate gene targets, wherein the ideal gene expression profile is a recommendation of gene expression for the set of candidate gene targets for maximizing, minimizing, or otherwise modulating the phenotype; and
instruction to use a gene editing system to make a genetic edit or perturbation to a genome of the plant based on the optimal set of genetic targets for editing each gene and the ideal gene expression profile.

9. The computer-program product of claim 8, wherein the explainable artificial intelligence system uses SHapley Additive explanations, DeepLIFT, integrated gradients, Local Interpretable Model-agnostic Explanations (LIME), Attention-Based Neural Network Models, or Layer-wise Relevance Propagation to analyze the decisions made by the prediction model.

10. The computer-program product of claim 8, wherein the one or more modeling approaches comprises: (i) modeling the gene edits by ascertaining directionality of regulation directly from the feature importance scores, (ii) modeling the gene edits using a Bayesian optimization algorithm, (iii) modeling the gene edits by performing adversarial attack on the prediction model, or (iv) any combination thereof.

11. The computer-program product of claim 8, wherein:
the explainable artificial intelligence system uses SHapley Additive explanations, which generates (i) a set of Shapley values as the feature importance scores for the features used in the prediction of the phenotype and (ii) correlations between the features and the phenotype;
the Shapley values represent estimates of each feature's importance as well as a direction; and
the gene edit modeling system models the gene edits by ascertaining directionality of regulation directly from the Shapley values, wherein the gene edit modeling system is configured to determine how candidate gene targets impact the phenotype through upregulation or downregulation based on the correlations.

12. The computer-program product of claim 8, wherein:
the prediction model is a Gaussian process model; and
the gene edit modeling system models the gene edits using a Bayesian optimization algorithm comprising two components: (i) the Gaussian process model of an underlying Gaussian process function, and (ii) an acquisition function for sampling various data points, wherein the Bayesian optimization algorithm is built based on a sequential search framework that incorporates both exploration and exploitation to direct a search to find a minimum or maximum of an objective function, and wherein the gene edit modeling system is configured to estimate a distribution of the underlying Gaussian process function at the features used in the prediction of the phenotype and use the distribution to direct the sampling by the acquisition function.

13. The computer-program product of claim 8, wherein:
the prediction model is a deep neural network; and
the gene edit modeling system models the gene edits by performing an adversarial attack on the deep neural network, the adversarial attack comprising freezing weights of the deep neural network, and optimizing over a space of constrained inputs to maximize or minimize the phenotype, wherein the optimizing comprises:
identifying the candidate gene targets;
defining an optimization problem for the deep neural network based on an optimal expression corresponding to a set of the candidate gene targets to maximize the phenotype;
defining constraints for gene expression based on the optimal expression; and
generating the optimal set of genetic targets by the adversarial attack.

14. The computer-program product of claim 8, wherein the actions further comprise:
comparing the ideal gene expression profile to a naturally occurring distribution of gene expression for the plant; and
determining a gene edit recommendation for upregulating or downregulating a particular gene, a sub group of genes, or each gene within the ideal gene expression profiles based on the comparing.

15. A system comprising:
one or more data processors; and
a non-transitory computer readable storage medium containing instructions which, when executed on the one or more data processors, cause the one or more data processors to perform actions including:
obtaining a set of gene expression profiles for a set of genes measured in a tissue sample of a plant;
inputting the set of gene expression profiles into a prediction model having a deep learning architecture constructed for a task of predicting a phenotype as output data by learning relationships or correlations between features of the set of gene expression profiles and the phenotype;
generating, using the prediction model, the prediction of the phenotype for the plant based on the relationships or the correlations between the features of the set of gene expression profiles and the phenotype;
analyzing, by an explainable artificial intelligence system, decisions made by the prediction model to predict the phenotype, wherein the analyzing comprises: (i) generating a set of feature importance scores for the features used in the prediction of the phenotype, wherein the feature importance scores represent estimates of each features contribution or influence on the prediction of the phenotype, and (ii) ranking or otherwise sorting the features based on the feature importance score associated with each of the features, wherein highest ranking or sorted features are identified as having a largest contribution or influence on the prediction of the phenotype;
identifying, based on the ranked or otherwise sorted features, a set of candidate gene targets for the phenotype as having the largest contribution or influence on the prediction of the phenotype;
inputting the set of candidate gene targets into a gene edit modeling system having an architecture constructed to model gene edits and generate ideal gene expression profiles for the phenotype using one or more modeling approaches and the set of candidate gene targets, wherein the one or more modeling approaches generate the ideal gene expression profiles based on the feature importance scores, an optimization algorithm, the prediction model, or any combination thereof;
generating, using the gene edit modeling system, an ideal gene expression profile for the phenotype based on an optimal set of genetic targets for editing of each gene within the set of candidate gene targets, wherein the ideal gene expression profile is a recommendation of gene expression for the set of candidate gene targets for maximizing, minimizing, or otherwise modulating the phenotype; and
instruction to use a gene editing system to make a genetic edit or perturbation to a genome of the plant based on the optimal set of genetic targets for editing each gene and the ideal gene expression profile.

16. The system of claim 15, wherein the one or more modeling approaches comprises: (i) modeling the gene edits by ascertaining directionality of regulation directly from the feature importance scores, (ii) modeling the gene edits using a Bayesian optimization algorithm, (iii) modeling the gene edits by performing adversarial attack on the prediction model, or (iv) any combination thereof.

17. The system of claim 15, wherein:
the explainable artificial intelligence system uses SHapley Additive explanations, which generates (i) a set of Shapley values as the feature importance scores for the features used in the prediction of the phenotype and (ii) correlations between the features and the phenotype;
the Shapley values represent estimates of each feature's importance as well as a direction; and
the gene edit modeling system models the gene edits by ascertaining directionality of regulation directly from the Shapley values, wherein the gene edit modeling system is configured to determine how candidate gene targets impact the phenotype through upregulation or downregulation based on the correlations.

18. The system of claim 15, wherein:
the prediction model is a Gaussian process model; and
the gene edit modeling system models the gene edits using a Bayesian optimization algorithm comprising two components: (i) the Gaussian process model of an underlying Gaussian process function, and (ii) an acquisition function for sampling various data points, wherein the Bayesian optimization algorithm is built based on a sequential search framework that incorporates both exploration and exploitation to direct a search to find a minimum or maximum of an objective function, and wherein the gene edit modeling system is configured to estimate a distribution of the underlying Gaussian process function at the features used in the prediction of the phenotype and use the distribution to direct the sampling by the acquisition function.

19. The system of claim 15, wherein:
the prediction model is a deep neural network; and
the gene edit modeling system models the gene edits by performing an adversarial attack on the deep neural network, the adversarial attack comprising freezing weights of the deep neural network, and optimizing over a space of constrained inputs to maximize or minimize the phenotype, wherein the optimizing comprises:
identifying the candidate gene targets;
defining an optimization problem for the deep neural network based on an optimal expression corresponding to a set of the candidate gene targets to maximize the phenotype;
defining constraints for gene expression based on the optimal expression; and
generating the optimal set of genetic targets by the adversarial attack.

20. The system of claim 15, wherein the actions further comprise:
comparing the ideal gene expression profile to a naturally occurring distribution of gene expression for the plant; and
determining a gene edit recommendation for upregulating or downregulating a particular gene, a sub group of genes, or each gene within the ideal gene expression profiles based on the comparing.

* * * * *